US005872011A

United States Patent [19]

Burley et al.

[11] Patent Number: 5,872,011

[45] Date of Patent: Feb. 16, 1999

[54] CRYSTAL OF A PROTEIN-LIGAND COMPLEX CONTAINING AN N-TERMINAL TRUNCATED EIF4E, AND METHODS OF USE THEREOF

[75] Inventors: Stephen K. Burley, New York, N.Y.; Nahum Sonenberg, Côte St-Luc, Canada; Joseph Marcotrigiano, New York, N.Y.; Anne-Claude Gingras, Montréal, Canada

[73] Assignees: The Rockefeller University, New York, N.Y.; McGill University, Montreal, Canada

[21] Appl. No.: 874,832

[22] Filed: Jun. 13, 1997

[51] Int. Cl.[6] ............................ G01N 30/50; C07K 14/00

[52] U.S. Cl. ............................................ 436/501; 530/350

[58] Field of Search ............................. 436/501; 530/350

[56] References Cited

U.S. PATENT DOCUMENTS

| | | | |
|---|---|---|---|
| 4,833,233 | 5/1989 | Carter | 530/363 |
| 5,322,933 | 6/1994 | Davies et al. | 530/399 |
| 5,525,711 | 6/1996 | Hawkins et al. | 536/22.1 |
| 5,554,522 | 9/1996 | Sacchettini et al. | 435/189 |
| 5,556,778 | 9/1996 | Sacchettini | 435/189 |
| 5,612,468 | 3/1997 | Hawkins et al. | 536/22.1 |

OTHER PUBLICATIONS

Adames et al.(1978) J. Biol. Chem. 253:2580–95.
Alexander et al.(1987)Mol. Cell Biol. 7:1436–44.
Altmann and Tranchsel(1989) Nucl. Acids Res. 17:5923–31.
Altmann et al.(1988) J. Biol. Chem. 263:17229–32.
Altmann et al.(1997) EMBO J. 16:1114–1121.
Altmann et al.(1989) J. Biol. Chem.264:12145–12147.
Belsham et al.(1996) Microbial Rev. 60:499–511.
Benoist and Chambon(1981) Nature 290:304–310.
Brunger(1993) Nature 355:472–5.
Bugg et al.(1993) Scientific American Dec.:92–98.
Cohen(1996) Structure 4:1013–6.
Darzynkiewicz et al.(1989) Biochemistry 28:4771–8.
Darzynkiewicz et al.(1988) Nucl. Acids Res. 16:8953–62.
Dunbrack et al.(1997) Folding & Design 2:R27–42.
Edery et al.(1988) Gene 74:517–25.
Friedland et al.(1996) Protein Science 6:125–31.
Furuichi et al.(1979) J. Biol. Chem. 254:6732–8.
Gilson et al.(1988) J. Comput. Chem. 9:327–335.
Haghighat et al.(1995) EMBO J. 14:5701–9.
Hendrickson(1991) Science 254:51–8.
Hodel et al.(1996) Cell 85:247–56.
Holm and Sander(1993) J. Mol. Biol. 233:123–38.
Ishida et al.(1991) J. Chem. Soc. Perkin Tans. I:1847–53.
Ishida et al.(1983) Biochemistry 22:3571–81.
Ishida et al.(1988) J. Amer. Chem. Soc. 110:2286–94.
Izaurralde et al.(1994) Cell 78:657–68.
Jones et al.(1996) Mol. Cell. Biol. 16:4754–64.
Jones et al. (1991) Acta Cryst. A47:110–9.
Joshi et al.(1995) J. Biol. Chem. 270:14597–603.
Kjeldgaard et al.(1996) FASEB J. 10:1347–68.
Lam et al.(1994) Science 263:380–384.
Lazaris–Karatzaz et al.(1990)Nature 345:544–7.
Laskowski et al.(1993) J. Appl. Cryst. 26:283–90.
Lin et al.(1994) Science 266:653–656.
Mader et al.(1995)Mol. Cell. Biol. 15:4990–7.
Manteuffel et al.(1996). Proc. Natl. Acad. Sci. USA 93:4076–80.
Marcotrigiano et al. (1997) Cell 89:1–20.
Minich et al.(1994)Proc. Natl. Acad. Sci. USA 91:7668–72.
Morino et al.(1996) Eur. J. Biochem. 239:597–601.
Nagai(1996) Curr. Opin. Struc. Biol. 6:53–61.
Nicholls et al.(1991) Proteins11:281–96.
Obrien, C. (1994) Science 266:542–3.
Oubridge et al.(1994) Nature 372:432–8.
Pause et al.(1994) Nature 371:762–7.
Proud, C.G. (1994) Nature 371:747–63.
Reich et al.(1995) Proc. Natl. Acad. Sci. USA 92:3298–3302.
Rhoads et al.(1983) Biochemistry 22:6084–88.
Rousseau et al.(1996) Oncogen 13:2415–20.
Sander and Schneider(1991) Proteins Struc. Funct. Genret. 9:56–68.
Sonenberg(1996) In Transkational Control eds. Hershey et al. 245–269, Cold Spring Harbor, NY: Cold spring Harbor-Laboratory Press.
Sonenberg(1979) Proc. Natl. Acad. Sci. USA 76:4345–9.
Sonenberg et al.(1996)Proc. Natl. Acad. Sci. USA 75:4843–7.
Svitkin et al.(1996) EMBO J. 15:7147–55.
Ueda et al.(1992) FEBS L. 280:207–10.
Ueda et al.(1992) J. Biochem. 109:882–9.
Valegard et al.(1994) Nature 371:623–6.
Vasilescu et al.(1996) J. Biol. Chem. 271:7030–7.
West et al.(1995) Tips16:67–74.
Whalen et al.(1996) J. Biol. Chem. 271:11831–7.
Wlodawer et al.(1993) Ann. Rev. Biochem. 62:543–85.

*Primary Examiner*—Charles L. Patterson, Jr.
*Attorney, Agent, or Firm*—Klauber & Jackson

[57] ABSTRACT

A detailed three-dimensional structure for the least abundant of the general translation initiation factors in eukaryotes, eIF4E, complexed with a ligand is disclosed. The novel N-terminal truncated eIF4Es which were constructed so as to omit a significant portion of the flexible N-terminal tail of the eIF4E are also part of the present invention. In addition, the crystals of the protein-ligand complexes containing the N-terminal truncated eIF4Es are also included. Furthermore, methods of identifying antagonists of the eIF4E protein which can be used to regulate protein synthesis in cells are also disclosed.

21 Claims, 6 Drawing Sheets

FIG.1A

```
                        40         50          60        70        80        90        100       110       120
                         |          |           |         |         |         |         |         |         |
Sec. Structure            SSSSS1SSSS              SSSS2SSSSHHHHHH1HHHH          SSS3SSS                 SSSS4SSS
Consensus               KHPLQN W LWF  KN  DKSK W  LR I  FDTVEDFWALYNHI  S L  G DYSLFK GIEPMWEDE NK GGRW ITLNK
Conserved                H L   W  W           W          F  VE FW     I       D   F     P WED     GG W
Function                                      s                                 r           sg        p
Environment             === = =        =   == =====  =  == = = = ==  == ==  = ===       = =  ==  = ==     = ===
Mouse       (36)        KHPLQNRWALWF-FKN--DKSKTWQANLRLISKFDTVEDFWALYNHIQLSSNLMPGCDYSLFKDGIEPMWEDEKNKRGGRWLITLNKQ
Human       (36)        KHPLQNRWALWF-FKN--DKSKTWQANLRLISKFDTVEDFWALYNHIQLSSNLMPGCDYSLFKDGIEPMWEDEKNKRGGRWLITLNKQ
Rat         (36)        KHPLQNRWALWF-FKN--DKSKTWQANLRLISKFDTVEDFWALYNHIQLSSNLMPGCDYSLFKDGIEPMWEDEKNKRGGRWLITLNKQ
Rabbit      (36)        KHPLQNRWALWF-FKN--DKSKTWQANLRLISKFDTVEDFWALYNHIQLSSNLMPGCDYSLFKDGIEPMWEDEKNKRGGRWLITLNKQ
Xenopus     (32)        KHPLQNRWALWF-FKN--DKSKTWQANLRLISKFDTVEDFWALYNHIQLSSNLMSGCDYSLFKDGIEPMWEDEKNKRGGRWLITLNKQ
Drosophila  (81)        KHPLMNVWTLWY-FKN--DRSKSWEDMQNEISKFDTVEDFWSLYNHIKPPSEIKLGSDYSLFKKNIRPMWEDAANKKGGRWVITLNK-
Yeast       (36)        KHPLNTKWTLWY-TKPAVDKSESWSDLLRPVTSFQTVEEFWAIIQNIPEPHELPLKSDYHVFRNDVRPEWEDEANAKGGKWSFQLR--
Pombe       (37)        KHPLARPWTLWF-LMPPTPGLE-WNELQKNIITFNSVEEFWGIHNNINPASSLPIKSDYSFFREGVRPEWEDVHNKTGGKWAFQNKG-
Wheat Germ  (32)        PHKLQRQWTFWYDIQTKPDKSKTWGTSLKKGYTFDTVEEFWCLYDQIFRPSKLVGSADFHLFKAGVEPKWEDPECANGGKWTVIS---
```

FIG.1B

```
                          130       140       150       160       170       180       190       200       210    217
                           |         |         |         |         |         |
Sec. Structure       HHHHHHHHH2HHHHHHHHHH       SSSS5SSSS SSSS6SSSS  HHHHHHHHH3HHHHHHH        SS7S HH4HH         SS8S
Consensus             R  DLD  WLETLLCLIGE FD  SD VCGAV NVR KGDKIAIWT  EN  A  HIG   KE L LP K VI YQ H DT  KSGS  K R  V
Conservation              D  WL        IGE  D       G V   R        WT              IG
Function                                               p    p   m                                              *
Environment           === = =  ==        ======      ===  =       = ====      ==  ==   =====      ===== ==== === =
Mouse       (121)    QRRSDLDRFWLETLLCLIGESFDDYSDDVCGAVVNVRAKGDKIAIWTTECENRDAVTHIGRVYKERLGLPPKIVIGYQSHADTATKSGSTTKNRFVV
Human       (121)    QRRSDLDRFWLETLLCLIGESFDDYSDDVCGAVVNVRAKGDKIAIWTTECENRDAVTHIGRVYKERLGLPPKIVIGYQSHADTATKSGSTTKNRFVV
Rat         (121)    QRRSDLDRFWLETLLCLIGESFDDYSDDVCGAVVNVRAKGDKIAIWTTECENRDAVTHIGRVYKERLGLPPKIVIGYQSHADTATKSGSTTKNRFVV
Rabbit      (121)    QRRSDLDRFWLETLLCLIGESFDDYSDDVCGAVVNVRAKGDKIAIWTTECENRDAVTHIGRVYKERLGLPPKIVIGYQSHADTATKSGSTTKNRFVV
Xenopus     (117)    QRRNDLDRFWLETLMCLIGESFDEHSDDVCGAVVNVRAKGDKIAIWTTEFENKDAVTHIGRVYKERLGLPAKVVIGYQSHADTATKSGSTTKNRFVV
Drosophila(164)      SSKTDLDNLWLDVLLCLIGEAFD-HSDQICGAVINIRGKSNKISIWTADGNNEEAALEIGHKLRDALRLGRNNSLQYQLHKDTMVKQGSNVKSIYTL
Yeast       (122)    GKGADIDELWLRTLLAVIGETIDEDDSQINGVVLSIRKGGNKFALWTKS-EDKEPLLRIGGKFKQVLKLTDDGHLEFFPHSSANGK---HPQPSITL
Pombe       (122)    RGGNALDEMWLTVLLAAIGETLDPTGQEVMGVVINMRKGFYRLAVWTKSCNNREVLMEIGTRFKQVLNLPRSETIEFSAHEDSSKKGSTRAKNRMSV
Wheat Germ(117)      SRKANLDTMWLETCMALIGEQFDE-SQEICGVVASVRQRQDKLSLWTKTASNEAVQVDIGKKWKEVIDYNDKMVYSFHDDSRSQKP---SRGGRYTV
```

Function:

w absolutely conserved tryptophan s π stacking tryptophan g hydrogen bond with guanine r stabilizing Arg157 p interactions with phosophate groups of 7-methyl-GDP m interaction with methyl group of 7-methyl-GDP

* site of phosphorylation in vivo at Ser209

Environment:

= indicates solvent accessible sidechain

CRYSTAL OF A PROTEIN-LIGAND COMPLEX CONTAINING AN N-TERMINAL TRUNCATED EIF4E, AND METHODS OF USE THEREOF

GOVERNMENTAL SUPPORT

The research leading to the present invention was supported, at least in part, by a grant from National Institutes of Health, Grant No. GM 07982. Accordingly, the Government may have certain rights in the invention.

FIELD OF THE INVENTION

The present invention relates to a form of the messenger RNA 5' cap-binding protein (eIF4E) that can be crystallized with a ligand to form a crystal with sufficient quality to allow detailed crystallographic data to be obtained. The crystals and the three-dimensional structural information are also included in the invention. In addition the present invention includes procedures for related structural based drug design based on the crystallographic data.

BACKGROUND OF THE INVENTION

Eukaryotic mRNA translation initiation is a complicated process involving assembly of a large protein-RNA complex that directs the ribosome to the initiation codon. Like transcription initiation, translation initiation represents a critical, rate-limiting step at which eukaryotic gene expression is regulated in response to developmental/environmental signals [reviewed in Mathews et al., "In *Translational Control*, eds. J. W. B. Hershey, M. B. Mathews, and N. Sonenberg. 1–29. Cold Spring Harbor, New York: Cold Spring Harbor Laboratory Press, (1996)]. For example, entry into and transit through the G1 phase of the cell cycle are correlated with increased rates of translation initiation [reviewed in Sonenberg et al., *Proc. Natl. Acad. Sci. USA,* 75:4843–4847 (1996)]. Eukaryotic mRNAs (excluding organellar mRNAs) are distinguished by the presence of a 5' cap structure and a 3' polyA tail that synergize in stimulating translation [reviewed in Shatkin, *Cell,* 9:645–653 (1976); Sachs and Wahle, *J. Biol. Chem.,* 268:22955–22958 (1993)]. The cap consists of guanosine, methylated at position 7, connected by a 5' to 5' triphosphate bridge to the first nucleotide of the mRNA [7-methyl-G(5') ppp(5')N, where N is any nucleotide].

In the most general case (cap-dependent translation), protein synthesis begins with recognition of 7-methyl-G(5') ppp(5')N by eukaryotic initiation factor 4E (eIF4E or cap-binding protein). eIF4E is the least abundant of the general translation initiation factors, and is considered to be the factor limiting recruitment of the ribosome to the translation start-site [reviewed in Sonenberg, In *Translational Control*, eds. J. W. B. Hershey, M. B. Mathews, and N. Sonenberg, 245–269, Cold Spring Harbor, NY: Cold Spring Harbor Laboratory (1996)]. Not surprising, overexpression of wild-type eIF4E in cultured cells causes malignant transformation [Lazaris-Karatzas et al., *Nature,* 345:544–547 (1990)]. eIF4E is a component of the eIF4F complex, which includes eIF4G (or p220) and eIF4A (an ATP-dependent RNA helicase). Biochemical studies revealed that eIF4G is a bridge between eIF4E and eIF4A [reviewed in Sonenberg, 1996, supra]. Following cap recognition by its eIF4E subunit, eIF4F and eIF4B unwind secondary structure in the 5'-untranslated region of the mRNA, rendering the initiation codon accessible to the ribosome [reviewed in Merrick and Hershey, In *Translational Control*, eds. J. W. B. Hershey, M. B. Mathews, and N. Sonenberg, 31–69, Cold Spring Harbor, New York: Cold Spring Harbor Laboratory Press (1996)]. Thus, cap-binding by eIF4E establishes a stable protein-mRNA foundation for assembly of a functional translation initiation complex.

Given eIF4E's pivotal role in translation, it is not surprising that it is a critically-important target for regulation of gene expression in eukaryotes. The transcriptional activator c-myc regulates eIF4E levels via interactions with an E-box in the eIF4E gene promoter [Jones et al., *Molec. Cell. Biol.,* 16:4754–4764 (1996)]. eIF4E activity is also regulated by post-translational modification, and by binding to negative regulators of translation initiation. In response to treatment of cells with growth factors, hormones and mitogens, 25 mammalian eIF4E is phosphorylated at Ser209 [Joshi et al., *J. Biol. Chem.,* 270:14597–14603 (1995); Whalen et al., *J. Biol. Chem.,* 271:11831–11837 (1996)]. Phosphorylation increases eIF4E affinity for mRNA caps, thereby stimulating translation initiation in vivo [reviewed in Sonenberg, 1996, supra]. Conversely, eIF4E activity is suppressed by 4E-binding proteins, such as mammalian 4E-BP 1, 4E-BP2 and 4E-BP3 [reviewed in Sonenberg, 1996, supra], and yeast p20 [Altmann et al., *EMBO J.,* 16:1114–1121 (1997)]. These negative regulators of gene expression have no effect on cap-binding, but instead block interactions between eIF4E and eIF4G [Mader et al., *Molec. Cell. Biol.,* 15:4990–4997 (1995); Haghighat et al., *EMBO J.,* 14:5701–5709 (1995); Altmann et al., 1997, supra]. Therefore, the 4E-binding proteins repress cap-dependent translation by inhibiting assembly of the eIF4F complex (eIF4E, eIF4G, and eIF4A). Insulin (as well as other hormones, mitogens and growth factors) increases protein synthesis, at least in part, by relieving the repressive effect of 4E-BP1 [Lin et al., *Science,* 266:653–656 (1994); Pause et al., *Nature,* 371:762–767 (1994)], via the phosphatidylinositol 3-kinase signal transduction pathway [Manteuffel et al., *Proc. Natl. Acad. Sci. USA,* 93:4076–4080 (1996)]. When 4E-BP1 is phosphorylated it no longer forms a stable complex with eIF4E, and binding of eIF4G and assembly of a functional translation initiation complex can resume [reviewed in Sonenberg, 1996, supra].

eIF4E has been the focus of considerable biochemical and genetic study. After its identification [Sonenberg et al., 1978, supra] and initial purification [Sonenberg et al., *Proc. Natl. Acad. Sci. USA,* 76:4345–4349 (1979)], cDNAs encoding eIF4E were cloned from various eukaryotes. Sequence comparisons revealed a phylogenetically-conserved 182 amino acid C-terminal portion (FIG. 1). In contrast, the N-terminus varies in length, shows little or no conservation among different organisms and is not required for cap-dependent translation in vitro (see below). Current structural knowledge of eIF4E is limited to results from site-directed mutagenesis (see below), and a photoaffinity labeling study [Friedland et al., *Protein Science,* 6: 125–131 (1996)]. The immediate challenge facing structural biologists interested in understanding translational regulation of gene expression is to establish the mechanistic and structural basis for eIF4E's interactions with the mRNA 5' cap, translation initiation factors, and regulatory proteins. This information is invaluable for the identification of methods of effecting these important translation initiation interactions, since translation initiation is a critical rate-limiting step in the regulation of eukaryotic gene expression response to developmental/environmental signals.

One such means of effecting the eIF4E protein and thereby, eukaryotic gene expression in general, is to identify agonists or antagonists to the eIF4E protein. Unfortunately, such identification has heretofore relied on serendipity and/ or systematic screening of large numbers of natural and synthetic compounds. A far superior method of drug-screening relies on structure based drug design. In this case, the three dimensional structure of a protein-inhibitor complex is determined and potential agonists and/or potential antagonists are designed with the aid of computer modeling [Bugg et al., *Scientific American*, December:92– 98 (1993); West et al., *TIPS,* 16:67–74 (1995); Dunbrack et al., *Folding & Design,* 2:27–42 (1997)]. However, heretofore the three-dimensional structure of the eIF4E protein has remained unknown, essentially because no eIF4E protein crystals had been produced of sufficient quality to allow the required X-ray crystallographic data to be obtained. Therefore, there is presently a need for obtaining a form of the eIF4E protein that can be crystallized with a ligand (such as an inhibitor) to form a crystal with sufficient quality to allow such crystallographic data to be obtained. Further, there is a need for such crystals. Furthermore there is a need for the determination of the three-dimensional structure of such crystals. Finally, there is a need for procedures for related structural based drug design based on such crystallographic data.

The citation of any reference herein should not be construed as an admission that such reference is available as "Prior Art" to the instant application.

SUMMARY OF THE INVENTION

The present invention provides detailed three-dimensional structural information for the least abundant of the general translation initiation factors in eukaryotes, eIF4E, complexed with a ligand. The present invention includes a modified form of the eIF4E protein, that is amenable to crystallization. In addition, the present invention provides crystals of protein-ligand complexes containing the eIF4E protein. The present invention also provides methods of identifying antagonists of the eIF4E protein which can be used to regulate protein synthesis in cells.

One aspect of the present invention is a crystal of a protein-ligand complex that comprises a protein-ligand complex of an N-terminal truncated eIF4E and a ligand. In one such embodiment the crystal effectively diffracts X-rays for the determination of the atomic coordinates of the protein-ligand complex to a resolution of greater than 5.0 Angstroms. In a preferred embodiment the crystal effectively diffracts X-rays for the determination of the atomic coordinates of the protein-ligand complex to a resolution of greater than 3.0 Angstroms. In a more preferred embodiment the crystal effectively diffracts X-rays for the determination of the atomic coordinates of the protein-ligand complex to a resolution of greater than 2.0 Angstroms. In the most preferred embodiment the crystal effectively diffracts X-rays for the determination of the atomic coordinates of the protein-ligand complex to a resolution of greater than 1.8 Angstroms.

The N-terminal truncated eIF4E of the present invention retains the globular core of the corresponding full-length of eIF4E (FIG. 1), which is required for the binding of eIF4E to 4E-BPs, cap recognition, and the stimulation of cap-dependent translation. These N-terminal truncated eIF4Es also lack all or a significant portion (minimally ten amino acids, preferably 20 amino acids, and more preferably 25 amino acids) of the flexible, proteolytically susceptible N-terminus. The N-terminal truncated eIF4Es can also have a methionine as the initial amino acid prior to the sequence, indicated.

In preferred embodiments the N-terminal truncated eIF4Es retain the conserved amino acids depicted in FIG. 1 and consist of approximately 170 to 200 amino acids. The N-terminal truncated eIF4E can be either phosphorylated (i.e., in mammals the serine that is reversibly phosphorylated in vivo is serine 209) or unphosphorylated. Similarly the N-terminal truncated eIF4E can comprise one or more selenomethionines substituted for a naturally occurring methionine of the corresponding full-length eIF4E. Of course, general modifications such as additional heavy atom derivatives common in X-ray crystallographic studies may also be performed on the N-terminal truncated eIF4E of the present invention and such modifications are also included as part of the present inventions.

In a preferred embodiment, the N-terminal truncated eIF4E is derived from a vertebrate eIF4E and lacks between 20 to 40 of the first forty N-terminal amino acids of the corresponding full-length eIF4E. In a more preferred embodiment, the N-terminal truncated eIF4E lacks between 25 to 35 of the first thirty-five N-terminal amino acids of the corresponding full-length eIF4E.

In one particular embodiment the N-terminal truncated eIF4E has an amino acid sequence of amino acids 28 to 217 of SEQ ID NO: 1, or an amino acid sequence that differs from amino acid 28 to 217 of SEQ ID NO: 1 by only having conservative substitutions. One such conservative substitution is the replacement of the aspartic acid at position 174 by a glutamic acid. In yet another particular embodiment the N-terminal truncated eIF4E has an amino acid sequence of amino acids 33 to 217 of SEQ ID NO: 1 or an amino acid sequence that differs from amino acid 33 to 217 of SEQ ID NO: 1 by only having conservative substitutions. Consistent with the description above, either of these embodiments can be phosphorylated at Serine 209, contain one or more selenomethionines in place of a methionine and/or be derivatized with a heavy metal atom.

In an alternative embodiment the N-terminal truncated eIF4E is derived from a drosophila eIF4E having an amino acid sequence of amino acids 72 to 262 of SEQ ID NO:6 or an amino acid sequence that differs from amino acid 72 to 262 of SEQ ID NO:6 by only having conservative substitutions.

The N-terminal truncated eIF4Es of the present invention can be derived from any eukaryotic source but is preferably a vertebrate eIF4E, more preferably from a mammalian eIF4E.

Any ligand that forms a complex with the N-terminal truncated eIF4E of the present invention can be used to form a crystal of the present invention. Preferably the ligand comprises an alkylated base. More preferably the ligand is 7-methyl guanosine diphosphate or derivative thereof.

A crystal of the present invention may take a variety of forms all of which are included in the present invention. In a preferred embodiment the crystal has a space group of $P2_12_12_1$ and the unit dimensions of a=59.3, b=74.8, and c=76.3. The N-terminal truncated eIF4E in the crystal has secondary structural elements that include three long α-helices, one short α-helix, and an eight-stranded, antiparallel β-sheet, arranged in the order: β-Sheet(1), β-Sheet(2), α-Helix(1), β-Sheet(3), β-Sheet(4), α-Helix(2), β-Sheet(5), β-Sheet(6), α-Helix(3), β-Sheet(7), α-Helix(4), β-Sheet(8) as depicted in FIG. 2C.

The present invention also includes nucleic acids encoding the N-terminal truncated eIF4Es of the present invention. In one particular embodiment the nucleic acid encodes an N-terminal truncated eIF4E having an amino acid sequence of amino acids 28 to 217 of SEQ ID NO: 1 or an amino acid sequence that differs from amino acid 28 to 217 of SEQ ID NO: 1 by only having conservative substitutions. In an alternative embodiment the nucleic acid encodes an N-terminal truncated eIF4E having an amino acid sequence of amino acids 33 to 217 of SEQ ID NO: 1 or an amino acid sequence that differs from amino acid 33 to 217 of SEQ ID NO: 1 by only having conservative substitutions. In still another embodiment the nucleic acid encodes an N-terminal truncated eIF4E having an amino acid sequence of amino acids 72 to 262 of SEQ ID NO:6 or an amino acid sequence that differs from amino acid 72 to 262 of SEQ ID NO:6 by only having conservative substitutions.

The present invention also provides expression vectors which comprise the nucleic acid of the present invention operatively associated with an expression control sequence. In a particular embodiment expression vector contains a nucleic acid encoding an N-terminal truncated eIF4E having an amino acid sequence of amino acids 28 to 217 of SEQ ID NO:1 or an amino acid sequence that differs from amino acid 28 to 217 of SEQ ID NO:1 by only having conservative substitutions. In an alternative embodiment the expression vector contains a nucleic acid encoding an N-terminal truncated eIF4E having an amino acid sequence of amino acids 33 to 217 of SEQ ID NO:1 or an amino acid sequence that differs from amino acid 33 to 217 of SEQ ID NO:1 by only having conservative substitutions. In still another embodiment the expression vector contains a nucleic acid encoding an N-terminal truncated eIF4E having an amino acid sequence of amino acids 72 to 262 of SEQ ID NO:6 or an amino acid sequence that differs from amino acid 72 to 262 of SEQ ID NO:6 by only having conservative substitutions.

The present invention further includes a cell transfected or transformed with an expression vector of the present invention. In one such embodiment the cell is a prokaryotic cell. In a preferred embodiment of this type the prokaryotic cell is an E. coli cell. In another embodiment the cell is a eukaryotic cell. In one such embodiment of this type the eukaryotic cell is an insect cell. In another such embodiment the eukaryotic cell is a vertebrate cell. In a preferred embodiment the vertebrate cell is a mammalian cell.

The present invention also includes methods of expressing the N-terminal truncated eIF4E comprising culturing a cell that expresses the N-terminal truncated eIF4E in an appropriate cell culture medium under conditions that provide for expression of the protein by the cell. Any of the cells mentioned above may be employed in this method. In a particular embodiment the cell is an E.coli cell which has been manipulated to express an N-terminal truncated eIF4E of the present invention. In a preferred embodiment, the method further includes the step of purifying the N-terminal truncated eIF4E.

The present invention further includes methods of using N-terminal truncated eIF4Es to grow a crystal of a protein-ligand complex. One such method comprises contacting an N-terminal truncated eIF4E with a ligand, wherein the N-terminal truncated eIF4E forms a protein-ligand complex with the ligand and then growing the crystal of the protein-ligand complex, wherein the crystal effectively diffracts X-rays for the determination of the atomic coordinates of the protein-ligand complex to a resolution of greater than 5.0 Angstroms. In a preferred embodiment the crystal effectively diffracts X-rays for the determination of the atomic coordinates of the protein-ligand complex to a resolution of greater than 3.0 Angstroms. In a more preferred embodiment the crystal effectively diffracts X-rays for the determination of the atomic coordinates of the protein-ligand complex to a resolution of greater than 2.0 Angstroms. In the most preferred embodiment the crystal effectively diffracts X-rays for the determination of the atomic coordinates of the protein-ligand complex to a resolution of greater than 1.8 Angstroms.

In a preferred method for growing the crystal, the growing of the crystal is performed by sitting-drop vapor diffusion. Standard micro and/or macro seeding may be used to obtain a crystal of X-ray quality, i.e. a crystal that will diffract to allow resolution greater than 5.0 Angstoms. Although any ligand for the N-terminal truncated eIF4E may be used, preferably the ligand comprises an alkylated base. Similarly in a preferred embodiment the N-terminal truncated eIF4e is either has an amino acid sequence of amino acids 28 to 217 of SEQ ID NO:1 or an amino acid sequence that differs from amino acid 28 to 217 of SEQ ID NO:1 by only having conservative substitutions or alternatively has an amino acid sequence of amino acids 33 to 217 of SEQ ID NO:1, or an amino acid sequence that differs from amino acid 33 to 217 of SEQ ID NO:1 by only having conservative substitutions.

Still another aspect of the present invention comprises a method of using a crystal of the present invention in a drug screening assay. In one such embodiment the method comprises selecting a potential ligand by performing rational drug design with a three-dimensional structure determined for the crystal, preferably in conjunction with computer modeling. Such computer modeling is preferably performed with a Docking program [Dunbrack et al., 1997, supra]. The potential ligand is then contacted with the ligand binding domain of eIF4E and the binding of the potential ligand and the ligand binding domain is detected. A potential ligand is selected as a potential drug on the basis of its binding to the ligand binding domain of eIF4E with a greater affinity for the ligand binding domain of eIF4E than a standard ligand, such as 7-methyl guanosine diphosphate.

In a preferred embodiment of this type, a supplemental crystal is grown which comprises a protein-ligand complex formed between an N-terminal truncated eIF4E and the potential drug. Preferably the crystal effectively diffracts X-rays for the determination of the atomic coordinates of the protein-ligand complex to a resolution of greater than 5.0 Angstroms, more preferably greater than 3.0 Angstroms, and even more preferably greater than 2.0 Angstroms. The three-dimensional structure of the supplemental crystal is determined by molecular replacement analysis or multi-wavelength anomalous dispersion of multiple isomorphous replacement. A candidate drug is selected by performing rational drug design with the three-dimensional structure determined for the supplemental crystal, preferably in conjunction with computer modeling. The candidate drug is then contacted with a cell that expresses eIF4E and a measure of protein synthesis is detected in the cell. A candidate drug is identified as a drug when it inhibits protein synthesis in the cell.

In an alternative embodiment, the present invention provides a method of using a crystal of the present invention in a drug screening assay to identify a candidate drug that inhibits protein synthesis. Such a method comprises the selection of a potential antagonist to an eIF4E by performing rational drug design with a three-dimensional structure determined for the crystal, preferably in conjunction with computer modeling. The potential antagonist is then is then added to a protein synthesis assay in which the eIF4E is a rate-limiting factor. A measure of protein synthesis is determined, and a potential agonist that inhibits that measure of protein synthesis is selected as a potential drug. The protein synthesis assay can be an in vitro, in situ or in vivo assay, but is preferably an in vitro assay. In one such embodiment of this type the assay is performed in a rabbit reticulocyte lysate using a capped mRNA encoding a marker protein.

In a preferred embodiment, a supplemental crystal is grown which comprises a protein-ligand complex formed between an N-terminal truncated eIF4E and the potential drug. Preferably the crystal effectively diffracts X-rays for the determination of the atomic coordinates of the protein-ligand complex to a resolution of greater than 5.0 Angstroms, more preferably greater than 3.0 Angstroms, and even more preferably greater than 2.0 Angstroms. The three-dimensional structure of the supplemental crystal is determined by molecular replacement analysis or multi-wavelength anomalous dispersion of multiple isomorphous replacement. A candidate drug is selected by performing rational drug design with the three-dimensional structure determined for the supplemental crystal, preferably in conjunction with computer modeling. The candidate drug is then contacted with a cell that expresses eIF4E. A candidate drug is identified as a drug when it inhibits protein synthesis in the cell.

In one embodiment the cell is a eukaryotic cell, including a yeast cell. In preferred embodiments the cell is a vertebrate cell. In more preferred embodiments the cell is a mammalian cell. In the most preferred embodiment the cell is a human cell. In one particular embodiment of this type, the potential drug is administered into an animal subject.

Such methods can further comprise an initial step consisting of determining the three-dimensional structure of a crystal comprising a protein-ligand complex formed between an N-terminal truncated eIF4E and a standard ligand for eIF4E, such as 7-methyl guanosine diphosphate, wherein the crystal effectively diffracts X-rays for the determination of the atomic coordinates of the protein-ligand complex to a resolution of greater than 5.0 Angstroms, more preferably greater than 3.0 Angstroms, and even more preferably greater than 2.0 Angstroms.

In one embodiment of this method the initial computer modeling is performed with one or more of the following docking computer modeling programs: DOC, GRAM and AUTO DOCK [Dunbrack et al., 1997, supra].

It should be understood that in all of the drug screening assays provided herein, a number of iterative cycles of any or all of the steps may be performed to optimize the selection.

In yet another aspect of the invention, the three-dimensional structure of a protein-ligand complex of an N-terminal truncated eIF4E (e.g., the murine eIF4E) and a ligand (e.g., the structure disclosed in the Example below) is used to determine the three-dimensional structure of a protein-ligand complex of a second N-terminal truncated eIF4E (e.g., a fungal eIF4E) and a ligand by computer analysis with a computer program that analyzes molecular structure and interactions. In one embodiment of this type the computer analysis is performed with one or more of the following computer programs: QUANTA, CHARMM, INSIGHT, SYBYL, MACROMODEL and ICM [Dunbrack et al., 1997, supra]. In a further embodiment of this aspect of the invention, an initial drug screening assay is performed using the three-dimensional structure so obtained, and along with a docking computer program. Such an initial drug screening assay is then performed with a classical drug screening assay using the biochemical assays described herein.

These and other aspects of the present invention will be better appreciated by reference to the following drawings and Detailed Description.

BRIEF DESCRIPTION OF THE DRAWINGS

FIG. 1 displays the sequence alignments of eIF4E from mouse [Altmann et al., *J. Biol. Chem.,* 264:12145–12147 (1989)], human [Rychlik et al., *Proc. Natl. Acad. Sci. USA,* 84:945–949 (1987)], rat [Miyagi et al., *Lab. Invest.,* 73:890–898 (1995)], rabbit [Rychlik and Rhoads, *Nucl. Acids Res.,* 20:6415 (1992)], Xenopus laevis [Wakiyama et al., *FEBS Letts.,* 360:191–193 (1995)], Drosophila melanogaster [Hernandez and Sierra, Biochim. Biophys. Acta, 1261:427–431 (1995)], Saccharomyces cerevisiae [Altmann et al., *Mol. Cell. Biol.,* 7:998–1003 (1987)], Schizosaccharomyces pombe [Ptushkina et al., *J. Biol. Chem.,* 271:32818–32824 (1996)], and wheat germ [Metz et al., *Nucleic Acids Res.,* 20:4096 (1992)], with their respective sequence numbers. The secondary structural elements were assigned from the X-ray structure. W indicates absolutely conserved tryptophan. Functional classifications: s, π stacking tryptophan; g, hydrogen bonded to guanine; r, stabilizing Arg157; p, interaction with phosphate groups of 7-methyl-GDP; m, van der Waals interaction with methyl group of 7-methyl-GDP; *, site of phosphorylation in vivo at Ser209. Environment classification: =, solvent accessible sidechain.

FIG. 3 shows the structure of the murine eIF4E-7-methyl-GDP complex.

FIG. 4 shows 7-methyl-GDP binding to eIF4E. Selected ligand atoms are labeled using lower case and italics to distinguish them from protein components.

FIG. 5 depicts the surface properties of eIF4E. GRASP [Nicholls et al., *Proteins,* 11:281–296 (1991)] representations of the chemical properties of the solvent accessible surface of eIF4E calculated using a water probe radius of 1.4 Å. For clarity, residues 28–35 have been omitted. The surface electrostatic potential is color coded red and blue, representing electrostatic potentials <–8 to >+8$k_BT$, where $k_B$ is the Boltzmann constant and T is the temperature. The calculations were performed with an ionic strength of 0 and dielectric constants of 80 and 2 for solvent and protein, respectively [Gilson et al., *J. Comput. Chem.,* 9:327–335 (1988)].

DETAILED DESCRIPTION OF THE INVENTION

Figure 2B:
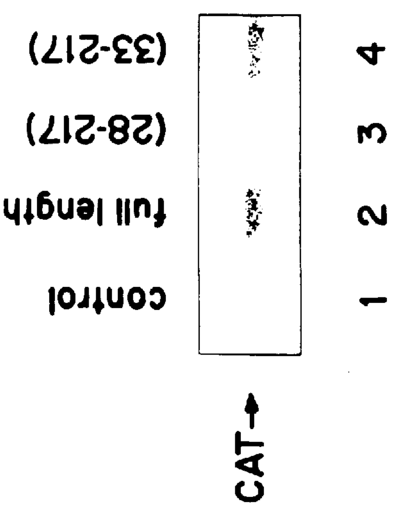
FIG. 2B shows the translation initiation assays comparing eIF4E (1–217), eIF4E(28–217) and eIF4E(33–217). The position of the translated CAT protein is indicated by an arrow.

The present invention provides crystals of a highly unusual protein-nucleotide complex. Furthermore, the present invention includes the three-dimensional structure derived from the analysis of the X-ray diffraction pattern of these crystals. Such analysis defines the 5' mRNA cap-binding properties of the least abundant of the general translation initiation factors in eukaryotes, eIF4E. The crystallographic information can be used to elucidate the role of eIF4E in translation initiation, and to a lessor extent the mechanisms by which eIF4E recognizes other translation initiation factors (i.e., eIF4G) and the 4E-binding proteins.

The present invention also provides methods of identifying antagonists of the eIF4E protein which can be used to regulate protein synthesis in cells. For example, small-molecule inhibitors of eukaryotic translation can be designed for use as drugs in the treatment of cancer, i.e., over-expression of eIF4E causes malignant transformation in cells in culture, and increased rates of translation are required to support cell division. Similarly, the structural information disclosed herein for the mammalian eIF4E can be used for gaining three-dimensional structural information for the corresponding eIF4E-ligand complex of unicellular eukaryotes, plants, and insects in conjunction with computer modeling using computer programs that analyze molecular structure and interactions for homologous proteins [Dunbrack et al., 1997, supra]. Such information can be used in the design of specific drugs for the treatment of parasitic infections (such as yeast or fungi) by inhibiting their eIF4Es, and thereby their protein synthesis, without inhibiting the corresponding mammalian protein, e.g., human eIF4E, or alternatively to remove unwanted plants, e.g., weeds or insects.

Therefore, if appearing herein, the following terms shall have the definitions set out below:

The "messenger RNA 5' cap-binding protein" or "cap-binding protein" is used herein interchangeably with "eukaryotic initiation factor 4E" or "eIF4E" and is the protein that binds to the 5' cap structure or 7-methyl-G(5')ppp(5')N of eukaryotic mRNAs. eIF4E is the least abundant of the general translation initiation factors, and is considered to be the factor that limits recruitment of the ribosome to the translation start-site. eIF4E is a component of the eIF4F complex, which includes eIF4G (or p220) and eIF4A (an ATP-dependent RNA helicase). The human eIF4E has the amino acid sequence of SEQ ID NO:2, whereas the murine eIF4E has the amino acid sequence of SEQ ID NO:1.

An "N-terminal truncated eIF4E" is an eIF4E that is missing a portion of its proteolytic susceptible N-terminus, but retains essentially all of the remaining proteolytic resistant globular structure of the protein. Minimally, the N-terminal truncated eIF4E is missing ten amino acids of the flexible, proteolytic susceptible N-terminus. The N-terminal truncated eIF4E can in addition to the sequence derived from the full length eIF4E, also contain a methionine as its N-terminus. Such an addition is generally not expressly stated in the identification of the N-terminus truncated protein. Thus an N-terminal truncated eIF4E having an amino acid sequence of amino acids 28–217 of SEQ ID NO:1 can have a methionine at its N-terminus and amino acid number 28 of SEQ ID NO:1 as the second amino acid residue. The N-terminal truncated eIF4E retains the globular core which is required for the binding of eIF4E to 4E-BPs, cap recognition and stimulation of cap-dependent translation. As can be seen in FIG. 1, this globular core region has striking homology across the entire spectrum of eukaryotes. This homology ensures that the structure of this region remains essentially constant throughout this spectrum. On the other hand, the flexible N-terminus is a much more variable region, which also varies substantially in length, e.g., the flexible N-terminus in humans is 35 amino acids long, whereas in drosophila it is approximately 80 amino acids long. The number of N-terminal amino acids which are needed to be removed to grow the crystals of the present invention, will vary accordingly. However, since the globular core remains relatively constant, the present invention provides a N-terminal truncated eIF4E which can be used to grow x-ray quality crystals, by the methods also provided herein, for an eIF4E of any eukaryote.

The "ligand binding domain of eIF4E" is the portion of eIF4E protein required for binding a nucleotide ligand. Minimally the ligand binding domain of eIF4E consists of a peptide containing that domain. However the use of this term is meant to include a ligand binding domain that is comprised by a larger portion of the eIF4E polypeptide, such as the N-terminal truncated eIF4E polypeptide, or the full-length eIF4E itself.

A "standard ligand for eIF4E" as used herein is a compound that has been shown to be a ligand for eIF4E such as 7-methyl guanosine diphosphate, 7-methyl guanosine triphosphate, and 7-methyl-G(5')ppp(5N) where N is any nucleotide.

A "protein synthesis assay" as used herein is an assay that can be performed in vitro, in situ (i.e., in an isolated cell) or in vivo in which "a measure of protein synthesis" can be determined. One simple assay is the use of an in vitro translation system. This can be a nuclease-treated reticulocyte lysate, or nuclease-treated translation extract prepared from nucleated cells (such as HeLa cells or Krebs 11 ascites). In these systems, exogenously added capped mRNA (synthesized in vitro in presence of a cap analog such as $m^7$GpppG) is allowed to be translated in presence of [35S] methionine and the potential antagonist. Added mRNA can be monocistronic (i.e. giving only one gene product) or bicistronic (encoding for two proteins). In the later, the DNA construct is built in such a way that the first cistron will be translated through a process called internal initiation [Belshaw et al., *Microbial Rev.,* 60:499–511 (1996)]. Therefore, comparing the translation of the first cistron (cap-dependent) versus the translation of the second cistron (cap-independent) gives an indication of the specific effects of eIF4E and the cap-dependent machinery. One such mRNA is CAT/EMC/LUC (chloramphicol acetyl transferase), followed by sequences directing internal initiation, followed by the reporter gene. Chloramphenicol acetyl transferase (CAT) and luciferase (LUC) activity can be monitored by standard methods. Alternatively, cells can be incubated in presence of [35S] methionine and the total incorporation of the radioactive label in proteins can be monitored. Cultured cell lines, such as HeLa cells or NIH 3T3 cells, are most suitable for the measure of protein synthesis via transfection of a reporter, since they are efficiently translated. [35S] labeling can be done on transformed or primary cells.

A "measure of protein synthesis" as used herein is any determination that can be made in which the synthesis of at least one protein can detected. One such measure is the detection of the amount of synthesis of a specific marker protein, e.g., measuring in vitro translation initiation activity in a rabbit reticulocyte lysate using a capped MRNA encoding a marker protein [described in Svitkin et al., *EMBO J.,* 15:7147–7155 (1996)] such as a capped chloramphenicol acetyl transferase (CAT) RNA. Analogous assays may be performed in situ with cells transfected with a nucleic acid encoding such a marker protein. Alternatively protein synthesis can be detected indirectly in vivo, for example as a function of tumor cell growth in a animal containing a tumor which over-expresses eIF4E as mentioned above.

A "rate-limiting factor" as used herein is a protein required for translation initiation in a cell and/or protein assay in which the rate of translation of at least one mRNA present in the cell and/or protein assay is dependent on the concentration of the functional "rate limiting factor". Therefore, inhibiting a rate limiting factor results in a corresponding decrease in the rate of translation of at least one mRNA present in the cell and/or protein assay.

Genes Encoding eIF4E Proteins

The present invention contemplates isolation of a gene encoding an eIF41, of the invention, including a full length, i.e., naturally occurring form of eIF4E from any eukaryote, and subsequent modification of that coding region of the gene to generate an N-terminal truncated eIF4E. As used herein, the term "gene" refers to an assembly of nucleotides that encode a polypeptide, and includes cDNA and genomic DNA nucleic acids.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in viva, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A "alkylated base" as used herein is an alkylated purine, pyrimidine, or pteridine.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamicle, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., *Cell,* 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

A gene encoding eIF4E, whether genomic DNA or cDNA, can be isolated from any source, particularly from a human cDNA or genomic library. In view and in conjunction with the present teachings, methods well known in the art, as described above can be used for obtaining eIF4E genes from any source [see, e.g., Sambrook et al., 1989, supra].

Accordingly, any animal cell potentially can serve as the nucleic acid source for the molecular cloning of an eIF4E gene. The DNA may be obtained by standard procedures known in the art from cloned DNA (e.g., a DNA "library"), and preferably is obtained from a cDNA library prepared from tissues with high level expression of the protein by chemical synthesis, by cDNA cloning, or by the cloning of genomic DNA, or fragments thereof, purified from the desired cell [See, for example, Sambrook et al., 1989, supra; Glover, D. M. (ed.), 1985, DNA Cloning: A Practical Approach, MRL Press, Ltd., Oxford, U.K. Vol. I, II]. Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The present invention also relates to cloning vectors containing genes encoding analogs and derivatives of eIF4Es including and more preferably the N-terminal truncated eIF4Es of the present invention, that have the same or homologous functional activity as eIF4E, and homologs thereof from other species. The production and use of derivatives and analogs related to eIF4E are within the scope of the present invention. The derivative or analog is functionally active, i.e., capable of exhibiting one or more functional activities associated with a full-length, wild-type eIF4E of the invention.

eIF4E derivatives can be made by altering encoding nucleic acid sequences by substitutions, additions or deletions that provide for functionally equivalent molecules. Preferably, derivatives are made that are capable of forming crystals of the protein-ligand complex that effectively diffract X-rays for the determination of the atomic coordinates of the protein-ligand complex to a resolution of greater than 5.0 Angstroms.

Due to the degeneracy of nucleotide coding sequences, other DNA sequences which encode substantially the same amino acid sequence as an eIF4E gene may be used in the practice of the present invention. These include but are not limited to allelic genes, homologous genes from other species, and nucleotide sequences comprising all or portions of eIF4E genes which are altered by the substitution of different codons that encode the same amino acid residue within the sequence, thus producing a silent change. Likewise, the eIF4E derivatives of the invention include, but are not limited to, those containing, as a primary amino acid sequence, all or part of the amino acid sequence of an eIF4E protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures arc phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free -OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The genes encoding eIF4E derivatives and analogs of the invention can be produced by various methods known in the art. The manipulations which result in their production can occur at the gene or protein level. For example, the cloned eIF4E gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of eIF4E, care should be taken to ensure that the modified gene remains within the same translational reading frame as the eIF4E gene, uninterrupted by translational stop signals, in the gene region where the desired activity is encoded.

Additionally, the eIF4E-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated eIF4E gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis [see Higuchi, 1989, "Using PCR to Engineer DNA", in *PCR Technology: Principles and Applications for DNA Amplification*, H. Erlich, ed., Stockton Press, Chapter 6, pp. 61–70].

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., E. coli, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences from the yeast 2 $\mu$ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of eIF4E

The nucleotide sequence coding for eIF4E, an N-terminal truncated eIF4E, derivative or analog thereof, or a functionally active derivative, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding eIF4E of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding eIF4E and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant eIF4E protein of the invention, or N-terminal truncated eIF4E, derivative, chimeric construct, or analog thereof, may be expressed chromosomally, after integration of the coding sequence by recombination. In this regard, any of a number of amplification systems may be used to achieve high levels of stable gene expression [See Sambrook et al., 1989, supra].

The cell containing the recombinant vector comprising the nucleic acid encoding eIF4E is cultured in an appropriate cell culture medium under conditions that provide for expression of eIF4E by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of eIF4E protein may be controlled by any promoter/enhancer element known in the art, but these regulatory elements must be functional in the host selected for expression. Promoters which may be used to control eIF4E gene expression include, but are not limited to, the SV40 early promoter region [Benoist and Chambon, *Nature,* 290:304–310 (1981)], the promoter contained in the 3' long terminal repeat of Rous sarcoma virus [Yamamoto et al., *Cell,* 22:787–797 (1980)], the herpes thymidine kinase promoter [Wagner et al., *Proc. Natl. Acad. Sci. U.S.A.,* 78:1441–1445 (1981)], the regulatory sequences of the metallothionein gene [Brinster et al., *Nature* 296:39–42 (1982)]; prokaryotic expression vectors such as the P-lactamase promoter [Villa-Kamaroff, et al., *Proc. Natl. Acad. Sci. U.S.A.,* 75:3727–3731 (1978)], or the tac promoter [DeBoer, et al., *Proc. Natl. Acad. Sci. U.S.A.,* 80:21–25 (1983)]; see also "Useful proteins from recombinant bacteria" in Scientific American, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., *Cell,* 38:639–646 (1984); Ornitz et al., *Cold Spring Harbor Symp. Quant. Biol.,* 50:399–409 (1986); MacDonald, *Hepatology,* 7:425–515 (1987)]; insulin gene control region which is active in pancreatic beta cells [Hanahan, *Nature,* 315:115–122 (1985)], immunoglobulin gene control region which is active in lymphoid cells [Grosschedl et al., *Cell,* 38:647–658 (1984); Adames et al., *Nature,* 318:533–538 (1985); Alexander et al., *Mol. Cell. Biol.,* 7:1436–1444 (1987)], mouse mammary tumor virus control region which is active in testicular, breast, lymphoid and mast cells [Leder et al., *Cell,* 45:485–495 (1986)], albumin gene control region which is active in liver [Pinkert et al., *Genes and Devel.,* 1:268–276 (1987)], alpha-fetoprotein gene control region which is active in liver [Krumlauf et al., *Mol. Cell. Biol.,* 5:1639–1648 (1985); Hammer et al., *Science,* 235:53–58 (1987)], alpha 1-antitrypsin gene control region which is active in the liver [Kelsey et al., *Genes and Devel.,* 1:161–171 (1987)], beta-globin gene control region which is active in myeloid cells [Mogram et al., *Nature,* 315:338–340 (1985); Kollias et al., *Cell,* 46:89–94 (1986)], myelin basic protein gene control region which is active in oligodendrocyte cells in the brain [Readhead et al., *Cell,* 48:703–712 (1987)], myosin light chain-2 gene control region which is active in skeletal muscle [Sani, *Nature,* 314:283–286 (1985) ], and gonadotropic releasing hormone gene control region which is active in the hypothalamus [Mason et al., *Science,* 234:1372–1378 (1986)].

Expression vectors containing a nucleic acid encoding an eIF4E of the invention can be identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding eIF4E is inserted within the "selection marker" gene sequence of the vector, recombinants containing the eIF4E insert can be identified by the absence of the eIF4E gene function. In the fourth approach, recombinant expression vectors can be identified by assaying for the activity, biochemical, or immunological characteristics of the gene product expressed by the recombinant, provided that the expressed protein assumes a functionally active conformation.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX [Smith et al., *Gene,* 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2$\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BanH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, *Current Protocols in Molecular Biology,* 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the eIF4E protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.,* 267:963–967 (1992); Wu and Wu, *J. Biol. Chem.,* 263:14621–14624 (1988); Hartmut et al., Canadian Patent Application No. 2,012,311, filed Mar. 15, 1990).

Peptide Synthesis

Synthetic polypeptides, prepared using the well known techniques of solid phase, liquid phase, or peptide condensation techniques, or any combination thereof, can include natural and unnatural amino acids. Amino acids used for peptide synthesis may be standard Boc ($N^{\alpha}$-amino protected $N^{\alpha}$-t-butyloxycarbonyl) amino acid resin with the standard deprotecting, neutralization, coupling and wash protocols of the original solid phase procedure of Merrifield [*J. Am.*

*Chem. Soc.,* 85:2149–2154 (1963)], or the base-labile $N^{\alpha}$-amino protected 9-fluorenylmethoxycarbonyl (Fmoc) amino acids first described by Carpino and Han [*J. Org. Chem.,* 37:3403–3409 (1972)]. Both Fmoc and Boc $N^{\alpha}$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^{\alpha}$-protecting groups that are familiar to those skilled in this art. Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, Int. J. Pept. Protein Res. 35:161–214, or using automated synthesizers. such as sold by ABS. Thus, polypeptides of the invention may comprise D-amino acids, a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, fluorophenylalanine for phenylalanine, and norleucine for leucine or isoleucine. Additionally, by assigning specific amino acids at specific coupling steps, α-helices, β turns, β sheets, γ-turns, and cyclic peptides can be generated.

Isolation and Crystallization of N-Terminal Truncated eIF4Es

The present invention provides N-terminal truncated eIF4Es that retain their ability to function as initiation factors and in addition can be crystallized with a ligand in a crystal that effectively diffracts X-rays for the determination of the atomic coordinates of the protein-ligand complex to a resolution of greater than 5.0 Angstroms. The N-terminal truncated eIF4Es of the present invention are constructed so as to have deleted most, if not all of the flexible portions of the eIF4E protein. These flexible portions are removed to prevent them from interfering with the crystallization of the protein. The N-terminal truncated eIF4Es of the present invention are also constructed to retain essentially all of the remaining globular portion of the protein. In the eIF4E having the amino acid sequence of SEQ ID NO:1, the first 35 amino acid residues of the 217 amino acid residue protein comprise the flexible portion of the protein whereas the remaining 182 amino acid residues (the "C-terminal" region) form the globular portion or globular core of the protein. Of course, the specific N-terminal truncated eIF4Es provided herein serve only as examples, since the crystallization process can tolerate a range of lengths of the flexible portion of the protein. Similarly, the crystallization process will also tolerate a limited removal of amino acids in the globular portion (e.g., less than ten amino acids). Therefore, any person with skill in the art of protein crystallization having the present teachings and without undue experimentation could construct a variety of alternative forms of the N-terminal truncated eIF4E which could be crystallized.

As mentioned above, N-terminal truncated eIF4Es having conservative substitutions in their amino acid sequence are also included in the invention including a selenomethionine substituted form, and a phosphorylated form of the protein, such as a phlosphorylated N-terminal truncated eIF4E corresponding to the eIF4E having the amino acid sequence of SEQ ID NO:1 containing a phosphoserine at Ser209. In addition, site-directed mutagenesis studies have elucidated certain primary structural requirements for eIF4E functionality [Morino et al., *Eur. J. Biochem.,* 239:597–601 (1996); Altmann et al., *J. Biol. Chem.,* 263:17229–17232 (1988); Altmann and Trachsel, *Nucl. Acids Res.,* 17:5923–5931 (1989) all of which are incorporated in their entireties herein] which can be used along with the three-dimensional structural information provided herein to design alternative N-terminal truncated eIF4Es.

Furthermore, certain amino acid residues, and in particular the 61 amino acid residues of the 182 C-terminal amino acids in which significant substitutions of the amino acids are shown in FIG. 1, can be more freely substituted than other amino acids in this conserved region. More specifically, those amino acid residues which map at the surface of an eIF4E, as defined by the structural information provided herein, will tolerate even non-conservative changes including in certain cases, deletions and insertions. N-terminal truncated eIF4Es containing such non-conservative changes are also included in the present invention. Thus the present invention is meant to include all forms of N-terminal truncated eIF4Es that retain their ability to perform as initiation factors and in addition are amenable to being crystallized with a ligand in a crystal that effectively diffracts X-rays for the determination of the atomic coordinates of the protein-ligand complex to a resolution of greater than 5.0 Angstroms.

The present invention also provides means of determining the flexible portions of a given eIF4E. For example, performing a limited proteolytic digest of a given full-length eIF4E can be very useful in determining the flexible portions of the protein. Proteolysis may be performed by a variety of proteases well known in the art, e.g., a V8 protease and subtilisin were used in the Example below. Mass spectrometry can be used to obtain accurate eIF4E cleavage maps [as described by Cohen, *Structure* 4:1013–1016 (1996)], although other methods of determination such as gel electrophoresis and/or amino acid sequencing can also be used.

The N-Terminal eIF4Es (plus an initiator methionine) can be expressed as described above. When expressed in E. coli, the protein is formed in an inclusion body. The N-terminal truncated protein can be solubilized with solubilization agents such as guanidinium (Gd) and urea and then renatured by dialysis. One such detailed protocol is provided in the Example below. The renatured proteins can be purified to homogeneity by 7-methyl-GDP affinity chromatography [Edery et al., *Gene,* 74:517–525 (1988)].

An N-terminal truncated eIF4E can be assayed to determine whether it can serve as a functional eIF4E by measuring translation initiation activity in an eIF4E-depleted rabbit reticulocyte lysate using a capped mRNA encoding a marker protein [described in Svitkin et al., *EMBO J.,* 15:7147–7155 (1996).] One such capped mRNA is a capped chloramphenicol acetyl transferase (CAT) RNA which can be synthesized by T7 RNA polymerase in the presence of a cap analogue such as 7-methyl-(5')Gppp(5')G.

Crystals of the N-terminal truncated eIF4E-ligand complex can be grown by a number of techniques including batch crystallization, vapor diffusion (either by sitting drop or hanging drop) and by microdialysis. Seeding of the crystals in some instances is required to obtain X-ray quality crystals. Standard micro and/or macro seeding of crystals may therefore be used. Exemplified below is the sitting-drop vapor diffusion procedure. In this example 100 mM 2-morpholinoethanesulfonic acid pH 6.0, 10–12% PEG 4K, 10% isopropanol, 20 mM dithiothreitol was used as the vapor diffusion buffer.

Once a crystal of the present invention is grown, X-ray diffraction data can be collected. The Example below used CHESS F1, under standard cryogenic conditions for such X-ray diffraction data collection though alternative methods may also be used. For example, crystals can be characterized by using X-rays produced in a conventional source (such as a sealed tube or a rotating anode) or using a synchrotron source. Methods of characterization include, but are not limited to, precision photography, oscillation photography and diffractometer data collection. Se-Met multiwavelength anomalous dispersion data [Hendrickson, *Science,* 254:51–58 (1991)] can be collected on CHESS F2, using reverse-beam geometry to record Friedel pairs at four X-ray wavelengths, corresponding to two remote points above and below the Se absorption edge ($\lambda_1$ and $\lambda_4$) and the absorption edge inflection point ($\lambda_2$) and peak ($\lambda_3$). Data can be processed using DENZO and SCALEPACK (Z. Otwinowski and W. Minor). Selenium sites can be located using SHELXS-90 in Patterson search mode (G. M. Sheldrick). Experimental phases ($\alpha_{MAD}$) can be estimated via a multiple isomorphous replacement/anomalous scattering strategy using MLPHARE (Z. Otwinowski, Southwestern University of Texas, Dallas) with three of the wavelengths treated as derivatives and one ($\lambda_2$) treated as the parent for example. Alternatively, X-PLOR [Brüger, X-PLOR v. 3.1 Manual, New Haven: Yale University, (1993B)] or Heavy [T. Terwilliger, Los Alamos National Laboratory] may be used. After density modification and non-crystallographic averaging, the protein is built into a electron density map using the program O [Jones et al., *Acta Cryst.*, A47: 110–119 (1991)]. Model building interspersed with positional and simulated annealing refinement [Brünger, 1993B, supra] can permit the location of the ligand e.g., 7-methyl-GDP and an unambiguous trace and sequence assignment of the N-terminal truncated eIF4E.

In the Example below, the current refinement model consists of eIF4E residues 36 to 207 and 212–217 plus 7-methyl-GDP (complex 1), and eIF4E residues 28 to 217 plus 7-methyl-GDP (complex 2), and 130 water molecules. All illustrations of eIF4E are derived from complex 2, with residues 28–35 omitted for clarity. The electron density for the polypeptide backbone is everywhere continuous at 1.3σ in a $(2|F_{observed}|-|F_{calculated}|)$ difference Fourier synthesis. PROCHECK [Laskowski et al., *J. Appl. Cryst.,* 26:283–290 (1993)] revealed 2/365 unfavorable (φ,ι) combinations, and main-chain and side-chain structural parameters consistently better than those expected at 2.2 Å resolution (overall G-factor=0.15).

Protein-Structure Based Design of Antagonists of eIF4E

Once the three-dimensional structure of a crystal comprising a protein-ligand complex formed between an N-terminal truncated eIF4E and a standard ligand for eIF4E is determined, a potential ligand is examined through the use of computer modeling using a docking program such as GRAM, DOCK, or AUTODOCK [Dunbrack et al., 1997, supra], to identify potential ligands and/or antagonists for eIF4E. This procedure can include computer fitting of potential ligands to the ligand binding site to ascertain how well the shape and the chemical structure of the potential ligand will complement the binding site. [Bugg et al., *Scientific American*, December:92–98 (1993); West et al., *TIPS,* 16:67–74 (1995)]. Computer programs can also be employed to estimate the attraction, repulsion, and steric hindrance of the two binding partners (i.e., the ligand-binding site and the potential ligand). Generally the tighter the fit, the lower the steric hindrances, and the greater the attractive forces, the more potent the potential drug since these properties are consistent with a tighter binding constant. Furthermore, the more specificity in the design of a potential drug the more likely that the drug will not interact as well with other proteins. This will minimize potential side-effects due to unwanted interactions with other proteins.

Initially potential ligands and/or agonists can be selected for their structural similarity to 7 -methyl-G(5')ppp(5')N [where N is any nucleotide], the natural binding partner to eIF4E. One such example is 7-methyl-guanosine diphosphate which was used in the Example below. The structural analog can then be systematically modified by computer modeling programs until one or more promising potential ligands are identified. Such analysis has been shown to be effective in the development of HIV protease inhibitors [Lam et al., *Science* 263:380–384 (1994); Wlodawer et al., *Ann. Rev. Biochem.* 62:543–585 (1993); Appelt, *Perspectives in Drug Discovery and Design* 1:23–48 (1993); Erickson, *Perspectives in Drug Discovery and Design* 1:109–128 (1993)]. Alternatively a potential ligand could be obtained by initially screening a random peptide library produced by recombinant bacteriophage for example, [Scott and Smith, *Science,* 249:386–390 (1990); Cwirla et al., *Proc. Natl. Acad. Sci.,* 87:6378–6382 (1990); Devlin et al., *Science,* 249:404–406 (1990)]. A peptide selected in this manner would then be systematically modified by computer modeling programs as described above, and then treated analogously to a structural analog as described below.

Another example of a structural analog of 7-methyl-G(5') ppp(5')N is 5-inethyl-pterin diphosphate. 5-methyl-pterin diphosphate is the pteridine nucleotide analog of 7-methyl-guanosine diphosphate [pteridine nucleotides have been defined by Hawkins et al., in U.S. Pat. Nos. 5,612,468 and 5,525,711, which are hereby incorporated by reference in their entireties]. Structurally, pteridines differ from the corresponding purine by containing an additional carbon in the heteronuclear ring structure, thereby having two six membered heteronuclear rings rather than the six membered-five membered heteronuclear ring system of a purine. The addition of the extra carbon in the corresponding pteridine nucleotide could have a significant effect on eIF4E-ligand binding, and such a pterin derivative could potentially lead to a potent eIF4E inhibitor. However, there are countless modifications of the 5-methyl-pterin that can be made, any one of which could lead to a useful drug. Each modification requires additional chemical steps, which while being reasonable for the synthesis of a few of these compounds, quickly becomes overwhelming if all of these compounds need to be synthesized. However, through the use of the three-dimensional structure disclosed herein and computer modeling, a large number of these compounds can be rapidly screened on the computer monitor screen, and a few likely candidates can be determined without the laborious synthesis of untold numbers of compounds.

Once a potential ligand or a potential antagonist is identified it can be either selected from a library of chemicals as are commercially available from most large chemical companies including Merck, GlaxoWelcome, Bristol Meyers Squib, Monsanto/Searle, Eli Lilly, Novartis and Pharmacia UpJohn, or alternatively the potential ligand or antagonist may be synthesized de novo. As mentioned above, the de novo synthesis of one or even a relatively small group of specific compounds is reasonable in the art of drug design. The potential ligand can be placed into a standard binding assay with the ligand binding domain of eIF4E. The ligand binding domain of an eIF4E can be synthesized by either standard peptide synthesis described above, or generated through recombinant DNA technology. Alternatively the N-terminal truncated eIF4Es or the corresponding full-length proteins may be used in these assays.

For example, the ligand binding domain of an eIF4E can be attached to a solid support. Methods for placing the ligand binding domain on the solid support are well known in the art and include such things as linking biotin to the ligand binding domain and linking avidin to the solid support. The solid support can be washed to remove unreacted species. A solution of a labeled potential ligand can be contacted with the solid support. The solid support is washed again to remove the potential ligand not bound to the support. The amount of labeled potential ligand remaining with the solid support and thereby bound to the ligand binding domain may be determined. Alternatively, or in addition, the dissociation constant between the labeled potential ligand and the ligand binding domain can be determined. Suitable labels are exemplified below.

In another aspect of the present invention a potential antagonist is assayed in a protein synthesis assay. One such assay entails measuring translation initiation activity in an eIF4E-depleted rabbit reticulocyte lysate using a capped mRNA encoding a marker protein [described in Svitkin et al., *EMBO J.* 15:7147–7155 (1996).] One such capped mRNA is a capped chloramphenicol acetyl transferase (CAT) RNA which can be synthesized by T7 RNA polymerase in the presence of a cap analogue such as 7-methyl-(5')Gppp(5')G.

A preferred assay employs an in vitro translation system. This can be, but is not restricted to, a nuclease-treated reticulocyte lysate, or nuclease-treated translation extract prepared from nucleated cells (such as HeLa cells or Krebs II ascites). In these systems, exogenously added capped mRNA (synthetized in vitro in presence of a cap analog such as $m^7$GpppG) is allowed to be translated in presence of [35S] methionine and the potential antagonist. Added mRNA can be monocistronic (i.e. giving only one gene product) or bicistronic (encoding two proteins). In the later case, the DNA construct is built in such a way that the first cistron will be translated by cap-dependent mechanism, and the second cistron will be translated through a process called internal initiation [Belsham et al., 1996, supra]. Therefore, comparing the translation of the first cistron (cap-dependent) versus the translation of the second cistron (cap-independent) gives an indication of the specific effects on eIF4E and the cap-dependent machinery. One such mRNA is CAT/EMC/LUC chloramphenicol acetyl transferase, followed by sequences directing internal initiation, followed by the luciferase reporter gene.

When suitable potential ligands and/or antagonists are identified, a supplemental crystal is grown which comprises a protein-ligand complex formed between an N-terminal truncated eIF4E and the potential drug. Preferably the crystal effectively diffracts X-rays for the determination of the atomic coordinates of the protein-ligand complex to a resolution of greater than 5.0 Angstroms, more preferably greater than 3.0 Angstroms, and even more preferably greater than 2.0 Angstroms. The three-dimensional structure of the supplemental crystal is determined by Molecular Replacement Analysis. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR (see above) and AMORE [J. Navaza, *Acta Crystallographics ASO,* 157–163 (1994)]. Once the position and orientation are known an electron density map can be calculated using the search model to provide X-ray phases. Thereafter, the electron density is inspected for structural differences and the search model is modified to conform to the new structure. Using this appoach, it will be possible to use the claimed structure of the mouse eIF4E to solve the three-dimensional structures of any eIF4E having a pre-ascertained amino acid sequence and/or corresponding eIF4E-ligand structures (e.g. containing 7-methyl-guanosine diphosphate). Other computer programs that can be used to solve the structures of the eIF4Es from other organisms include: QUANTA, CHARMM; INSIGHT; SYBYL; MACROMODE; and ICM.

A candidate drug is selected by performing rational drug design with the three-dimensional structure determined for the supplemental crystal, preferably in conjunction with computer modeling discussed above. The candidate drug is then contacted with a cell that expresses eIF4E. A candidate drug is identified as a drug when it inhibits protein synthesis in the cell. The cell can be either isolated from an animal, including a transformed cultured cell; or alternatively, in a living animal. Preferably the cell is an isolated cell. Suitable cells for performing such assays include HeLa cells and NIH/3TC cells.

One measure of protein synthesis can be effected by transfecting the cells with a reporter gene, preferably but not necessarily bicistronic. One such a reporter is CAT/EMC/LUC. Choloramphenicol acetyl transferase (CAT) and luciferase (LUC) activity can be monitored by standard methods. Alternatively, cells can be incubated in the presence of [35S] methionine and the total incorporation of the radioactive label in proteins can be monitored. Cultured cell lines, such as HeLa cells or NIH 3T3 cells, are most suitable for the measure of protein synthesis via transfection of a reporter, since they are effeciently translated. [35S] labeling can be done on transformed or primary cells. A drug can also be tested for anti tumor activity as described by Rousseau et al. [*Oncogene,* 13:2415–2420 (1996)].

For all of the drug screening assays described herein further refinements to the structure of the drug will generally be necessary and can be made by the successive iterations of any and/or all of the steps provided by the particular drug screening assay.

Labels

Suitable labels include enzymes, fluorophores (e.g., fluorescene isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme. detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70:419–439 (1980) and in U.S. Pat. No. 4,857,453.

Suitable enzymes include, but are not limited to, alkaline phosphatase and horseradish peroxidase. Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Patent No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $1^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^{3}H]$-amino acids (with the tritium substituted at non-labile positions).

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE

Cocrystal Structure of the Messenger RNA 5' Cap-Binding Protein (eIF4E) Bound to 7-Methyl-Gdp

Introduction

The 2.2Å resolution X-ray structure of the mRNA 5' cap-binding protein murine 4E (eIF4E) bound to a cap analogue (7-methyl-GDP) is disclosed. eIF4E recognizes 5' 7-methyl-G(5')ppp(5')N mRNA caps during the rate-limiting initiation step of translation. This work provides the first structure of a eukaryotic translation initiation factor, and of a protein recognizing an alkylated base. The α/β protein resembles a cupped hand, and consists of a curved, antiparallel 8-stranded β-sheet backed by three long cc-helices. The concave basal surface contains a narrow cap-binding slot, where the sidechains of two conserved tryptophans support recognition of 7-methyl-GDP. Guanine recognition is mediated by three hydrogen bonds, involving a backbone amino group and the sidechain of a conserved glutamate, and a van der Waals contact with another conserved tryptophan. The convex dorsal surface of the molecule displays a phylogenetically-conserved hydrophobic/acidic portion, which may interact with other translation initiation factors and regulatory proteins. The structural analysis described herein explains how elF4E can recognize the mRNA 5' cap during the first step of translation initiation in eukaryotes

Experimental Procedures

Protein Preparation and Crystallization:

Full-length murine mRNA 5' cap-binding protein [eIF4E (1–217)] was expressed in E. coli, and purified to homogeneity via 7-methyl-GDP affinity chromatography (Edery et al. 1988). Mass spectrometry documented that purified eIF4E(1–217) was neither modified nor proteolyzed. Initial crystallization trials immediately yielded needles, which resisted attempts to improve their size. Reasoning that a flexible portion or portions of the protein might be interfering with crystallization, a proteolytic limit digest of eIF4E (1–217) was performed. Proteolysis with V8 protease and subtilisin was combined with mass spectrometry to obtain accurate eIF4E cleavage maps using the methods reviewed in Cohen 1996.

eIF4E(28–217) plus an initiator methionine was expressed in E. coli as inclusion bodies. Guanidinium-solubilized eIF4E(28–217) was renatured by dialysis, and purified. A one liter culture of E. coli containing a DNA construct encoding the N-terminal truncated eIF4E was grown and induced at 37° C. to maximize the amount of protein formed in the inclusion bodies. The cells were harvested and resuspended in 20 ml of 20 mMHepes pH 7.5 containing 100 mM KCl, 0.5 mM EDTA, 5 mM DTT and 10% glycerol [Buffer A]. The cells were lysed with a French press, the lysate was pelleted, and the supernatent was discarded. The pellet was then washed three or more times by the following procedure: 5 to 10 ml of 20 mM Hepes pH 7.5 containing 1M guanidinium-hydrochloride (Gd-HCl) and 10% glycerol was added to the pellet (just enough to cover the pellet), the pellet was resuspended by sonication, centrifuged and the supernatent was discarded.

The washed pellet was resuspended in 10 ml of 20 mM Hepes pH 7.5 containing 6M Gd-HCl and 10% glycerol [Buffer C], sonicated, and then centrifuged. This time the supernatent was kept and the pellet was discarded. The protein concentration was determined (BioRad protein assay) and the protein was diluted with Buffer C to a final concentration of ≦0.5 mg/ml. The diluted protein was then dialyzed against Buffer A minus glycerol. The dialized protein was then centrifuged to removed misfolded protein (which precipitates). The centrifuged protein was then filtered through a 1.2 uM filter and purified as described by Edery et al. [*Gene,* 74:517–525 (1988)].

The measured molecular mass for eIF4E(28–217) was 22,117±5 (predicted 22,113). Dynamic light scattering, performed with a DynaPro-801 Molecular Size Detector (Protein Solutions Inc., Charlottesville, Va.), demonstrated that eIF4E(28-217) was monomeric and monodisperse at 1 mg/ml in aqueous solution. Crystallization trials yielded crystals in the orthorhombic space group $P2_12_12_1$ (a=59.3 Å, b=74.8 Å, c=76.3 Å), with two protein-ligand complexes in the asymmetric unit that diffract to at least 1.8 Å resolution. eIF4E(28–217)-7-methyl-GDP cocrystals were grown by sitting-drop vapor diffusion against 100 mM 2-morpholinoethanesulfonic acid pH 6.0, 10–12% PEG 4K, 10% isopropanol, 20 mM dithiothreitol. eIF4E(28–217) was also expressed in its selenomethionine (Se-Met) substituted form and the Se-Met protein was purified, characterized by mass spectrometry and crystallized as above. eIF4E (33–217) was also produced and purified to homogeneity as described above.

Translation Initiation Assays:

Capped chloramphenicol acetyl transferase (CAT) RNA was synthesized by T7 RNA polymerase in the presence of the cap analogue 7-methyl-(5')Gppp(5')G. Recombinant eIF4Es (full-length, 28–217, 33–217) were assayed for translation initiation activity in an eIF4E-depleted rabbit reticulocyte lysate as described in Svitkin et al. 1996.

Data Collection, Structure Determination and Refinement:

Native X-ray diffraction data were collected on CHESS F1, under standard cryogenic conditions. Se-Met multi-wavelength anomalous dispersion data [Hendrickson, 1991, supra] were collected on CHESS F2, using reverse-beam geometry to record Friedel pairs at four X-ray wavelengths, corresponding to two remote points above and below the Se absorption edge ($\lambda_1$ and $\lambda_4$) and the absorption edge inflection point ($\lambda_2$) and peak ($\lambda_3$). Data were processed using DENZO and SCALEPACK (Z. Otwinowski and W. Minor). Four of the possible six selenium sites were found using SHELXS-90 in Patterson search mode (G. M. Sheldrick). Experimental phases ($\alpha_{MAD}$) were estimated at 2.5 Å resolution via a multiple isomorphous replacement/anomalous scattering strategy using MLPHARE (Z. Otwinowski) with three of the wavelengths treated as derivatives and one ($\lambda_2$) treated as the parent, giving a final figure of merit of 0.52. The resulting $|F_{observed}|/\alpha_{MAD}$ Fourier map showed good contrast between solvent and protein regions, with right-handed a-helices and β-strands clearly visible. After density modification and two-fold non-crystallographic averaging, about 95% of the residues could be built into the electron density map using the program O [Jones et al., 1991, supra]. Model building interspersed with positional and simulated annealing refinement [Brünger, 1993B, supra] permitted location of 7-methyl-GDP and an unambiguous trace and sequence assignment of eIF4E.

The current refinement model consists of eIF4E residues 36 to 207 and 212–217 plus 7-methyl-GDP (complex 1), and eIF4E residues 28 to 217 plus 7-methyl-GDP (complex 2), and 130 water molecules. All illustrations of eIF4E are derived from complex 2, with residues 28–35 omitted for clarity. The electron density for the polypeptide backbone is everywhere continuous at 1.3σ in a $(2|F_{observed}|-|F_{calculated}|)$ difference Fourier synthesis. PROCHECK [Laskowski et al., 1993, supra] revealed 2/365 unfavorable (φ,ι) combinations, and main-chain and side-chain structural parameters consistently better than those expected at 2.2 Å resolution (overall G-factor=0.15).

Results

Figure 2A:
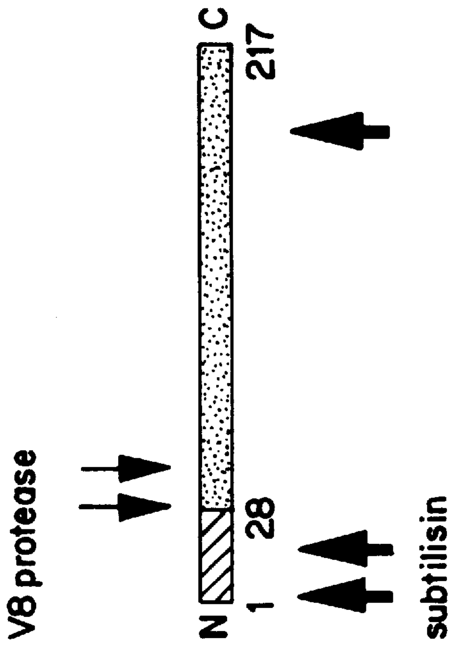
FIG. 2A depicts the proteolysis of the eIF4E(1–217)-7-methyl-GDP complex. V8 protease and subtilisin were used to probe the domain structure of eIF4E [Cohen, *Structure,* 4:1013–1016 (1996)]. The polypeptide chain is represented schematically (the solid portion represents the N- and C-terminal limits of the construct used for structure determination), with large arrows denoting cleavage sites observed within minutes to hours and small arrows denoting cleavage sites observed between 4 and 24 hrs.

Conserved C-terminus of eIF4E Supports Translation Initiation and Binding to 4E-BP1:

FIG. 2A illustrates the results of mass spectrometry of full-length murine eIF4E following protease digestion. This combination of classical biochemistry and high-resolution mass spectrometry is extremely useful for identifying domains within proteins [reviewed in Cohen, 1996, supra]. The majority of the V8 protease and subtilisin cleavage sites in eIF4E map to its divergent N-terminus (FIG. 2A), suggesting that the conserved C-terminal portion corresponds to a proteolytically-resistant globular structure. This C-terminal portion is essentially identical for all sequences of mammalian eIF4Es that have been determined (FIG. 1).

Earlier studies in Saccharomyces cerevisiae had shown that deletion of the first 29 residues of the yeast eIF4E yielded a protein that supported growth of eIF4E-deficient yeast [Vasilescu et al., *J. Biol. Chem.,* 271:7030–7037 (1996)]. Since full-length murine eIF4E can substitute for its yeast counterpart in vivo [Altmann et al., 1989, supra] it was envisioned that the N-terminal truncation of a mammalian protein would also lead to a functioning modified protein. Indeed, the N-terminal truncation of murine eIF4E [eIF4E (28–217)] yields a functionally active protein (FIG. 2B). This form of eIF4E also binds to the cap structure with the same affinity as the full-length protein and interacts with 4E-BP1. Furthermore, the eIF4E(33–217) murine N-terminal truncated protein was also functional. Together, these data suggest that the divergent N-terminal portion of eIF4E is dispensable for cap recognition, binding to the 4E-BPs, and stimulation of cap-dependent translation. At present, there is no known function for the N-terminus of eIF4E in any eukaryote.

Crystallization and Structure Determination: eIF4E (28–217) yielded high-quality cocrystals with 7-methyl-GDP, which contain two crystallographically-independent copies of the 1:1 protein-ligand complex in the asymmetric unit (see Experimental Procedures). The eIF4E-7-methyl-GDP complex structure was determined via multiwavelength anomalous dispersion [Hendrickson, 1991, supra] (Table 1). Experimental phases obtained at 2.5 Å resolution gave a high-quality electron density map, which was further improved by density modification, non-crystallographic averaging and phase combination. The current refinement model has an R factor of 20.9% and a free R value of 27.7% [Brünger, *Nature,* 355:472–475 (1993A)] at 2.2 Å resolution.

TABLE 1

Statistics of the crystallographic analysis

| Data Set | Resolution (Å) | Reflections measured/unique | Completeness (%) overall/outer shell | $R_{sym}$ (%) overall/outer shell | Phasing power |
|---|---|---|---|---|---|
| MAD analysis (5 Se sites) | | | | | |
| λ1(0.987 Å) | 25.0-2.5 | 187,450/13,769 | 95.7/90.0 | 5.7/12.1 | 0.78 |
| λ2(0.979 Å) | 25.0-2.5 | 190,172/13,758 | 96.1/95.3 | 5.4/11.3 | 0.00 |
| λ3(0.978 Å) | 25.0-2.5 | 190,235/13,767 | 95.9/95.4 | 5.5/11.3 | 0.25 |
| λ4(0.968 Å) | 25.0-2.5 | 189,470/13,749 | 95.9/95.4 | 5.4/11.0 | 0.84 |
| Overall MAD figure of merit, 0.52 | | | | | |
| Native Data | 25.0-2.2 | 289,102/20,212 | 99.8/99.8 | 8.6/24.8 | |

TABLE 1-continued

| Statistics of the crystallographic analysis | | | | |
|---|---|---|---|---|
| Refinement Statistics | Resolution (Å) | Completeness (%) | R-factor overall/outer shell | Free R-factor |
| Data with [F] > 2σ (\|F\|) | 25.0-2.2 | 99.8 | 0.209/0.235 | 0.277 |
| R.m.s. deviations | Bond lengths, 0.014 Å | Bond angles, 2.1° | Thermal parameters, 1.4 $Å^2$ | |

Table 1 Footnotes:
$R_{sym} = \Sigma|I - \langle I \rangle|/\Sigma I$, where I = observed intensity, $\langle I \rangle$ = average intensity obtained from multiple observations of symmetry related reflections.
Phasing power = r.m.s.($|F_H|$/E), $|F_H|$ = heavy atom structure factor amplitude and E = residual lack of closure.
r.m.s bond lengths and r.m.s. bond angles are the respective root-mean-square deviations from ideal values. r.m.s. thermal parameter is the root-mean-square deviation between the B values of covalently bonded atomic pairs.
Free R-factor was calculated with 10% of data omitted from the structure refinement.

Figure 2C:
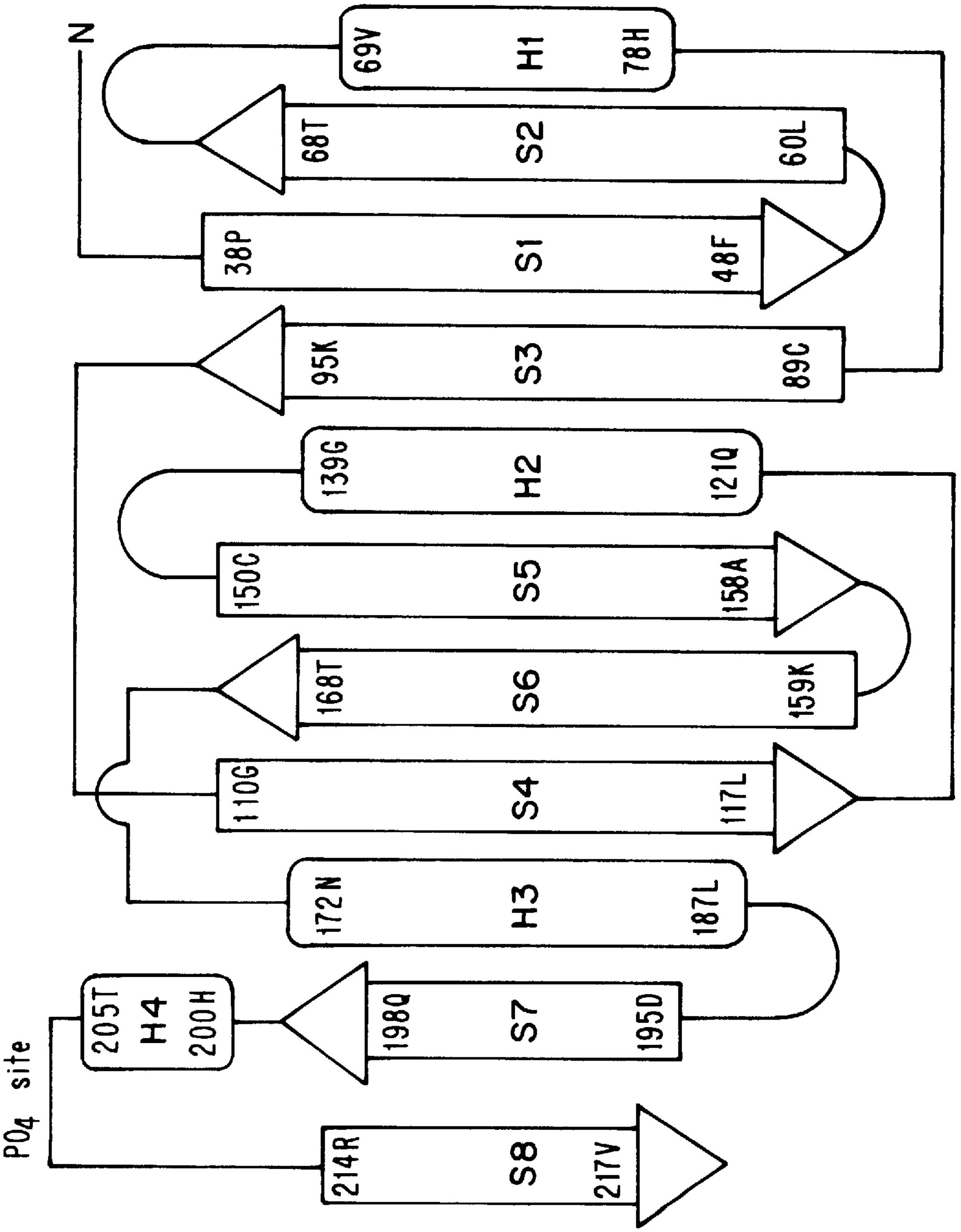
FIG. 2C is a schematic drawing of the secondary structure of murine eIF4E(28–217). α-helices (H) are shown as rectangles and β-strands (S) are shown as arrows, with the residues numbers denoting the limits of each secondary structural element.
Figure 3A:
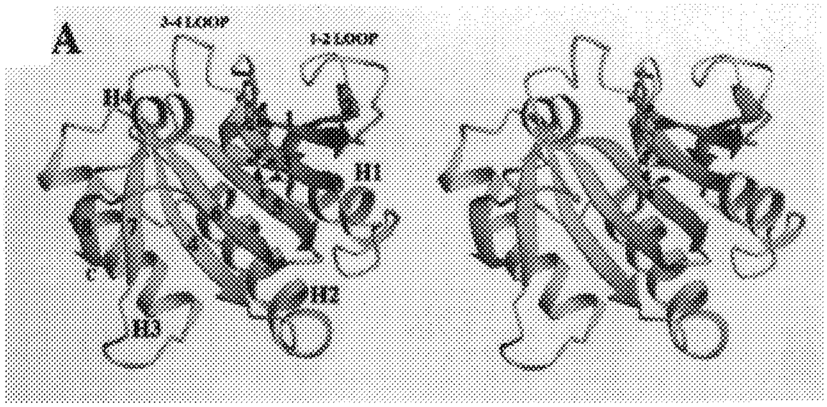
FIG. 3A depicts the RIBBONS [Carson, *J. Appl. Cryst.,* 24:958–961 (1991)] stereodrawing showing the concave cap-binding surface of eIF4E(28–217). 7-methyl-GDP, included as an atomic stick figure, is located in the cap-binding slot. α-helices are labeled H1–H4 and β-strands are labeled 1–8, with the N- and C-termini labeled with N and C, respectively. The 5'-untranslated region of the mRNA would presumably project down and left to the entrance of the cap-binding slot, overlying helix H3 and strands S5, S6 and S4.
Figure 3B:
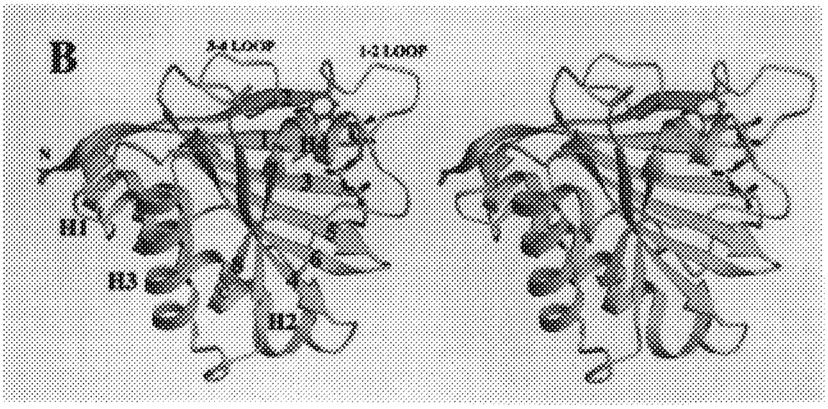
FIG. 3B is a stereo drawing viewed along the face of the β-sheet, showing eIF4E in profile and the location of the α-helices on the molecule's convex dorsal surface.
Figure 3C:
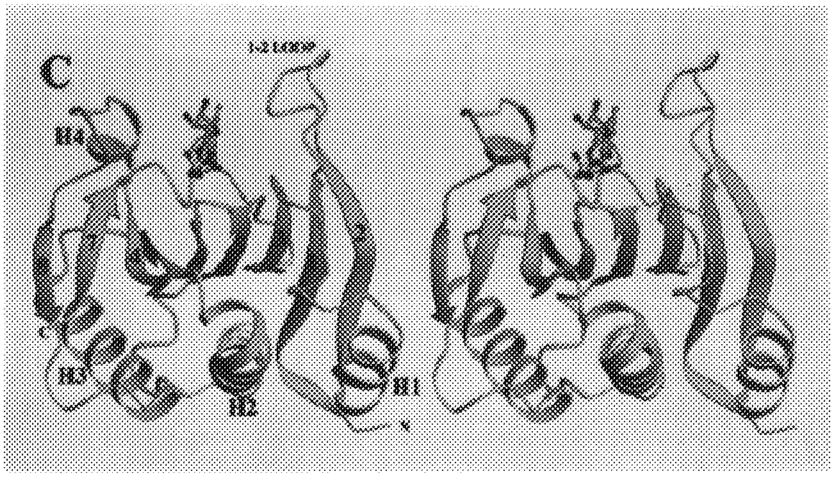
FIG. 3C is a stereo drawing viewed along the face of the β-sheet, showing 7-methyl-GDP and the entrance to the cap-binding slot.
Figure 3D:
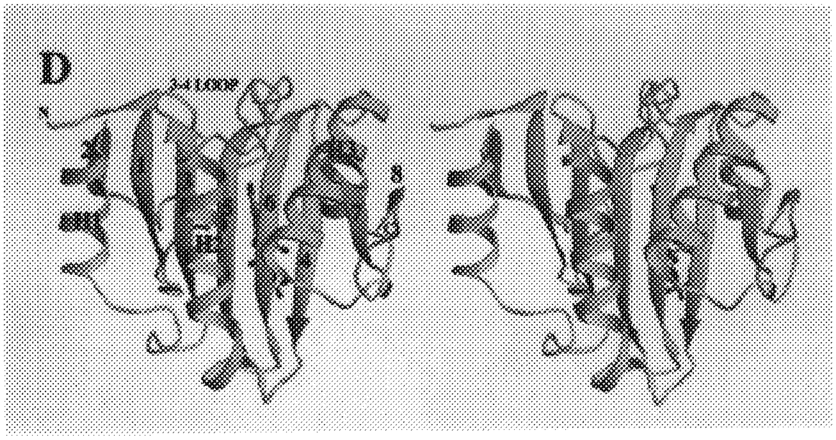
FIG. 3D is a stereo drawing viewed perpendicular to the β-strands, showing the convex dorsal surface of eIF4E with its three long α-helices.

Structural Overview: The three-dimensional structure of eIF4E is illustrated schematically in FIGS. 2C and 3. The molecule is shaped like a cupped hand with dimensions 41 Å(width)×36 Å(height)×45 Å(depth), and consists of one α/β domain. Secondary structural elements include three long and one short a-helices and an 8-stranded, antiparallel β-sheet, arranged in the order S1-S2-H1-S3-S4-H2-S5-S6-H3-S7-H4-S8 (FIG. 2C). FIGS. 3A–D show the eIF4E fold with its 7-methyl-GDP ligand. The 8 β-strands are arranged in space in the order S2-S1-S3-S5-S6-S4-S7-S8, making a curved, antiparallel β-sheet (FIGS. 3A–B). The three long α-helices (H1, H2 and H3) lie almost parallel to the strand direction, and top the β-sheet (FIGS. 3C–D). The narrow ligand-binding cleft (cap-binding slot) is generated by the concave surface of the β-sheet, the short a-helix (H4), and the loop between strands S1 and S2. It is closed at one end by the loop connecting strands S3 and S4, and open at the other (FIGS. 3A–C).

The two eIF4E-7-methyl-GDP complexes comprising the crystallographic asymmetric unit are related by a noncrystallographic two-fold rotation. They are very similar, with root-mean-square (r.m.s.) deviations between α-carbon atomic positions of 0.5 Å. Packing interactions between the complexes are mediated by salt bridges, hydrogen bonds and van der Waals interactions. Hydrodynamic studies of murine eIF4E(28–217) showed that it is monomeric in solution at concentrations of about 1 mg/ml in aqueous solution (see Experimental Procedures).

The N-terminal truncated eIF4E(28–217) represents a new protein fold. A search using the Dali server [Holm and Sander, *J. Mol. Biol.,* 233:123–138 (1993)] revealed a maximum Z-score of 4.1, obtained with an unrelated α/β protein (D-3-phosphoglycerate dehydrogenase, sPDB Accession Code 1PSD-B). It is remarkable that the prokaryotic ribosomal protein S6 (PDB Accession Code 1RIS), which is composed of two α-helices topping a four-stranded antiparallel β-sheet, gave a Z-score of 3.2. Comparison of the structure of eIF4E with that of VP39 [Hodel et al., *Cell,* 85:247–256 (1996)] suggests that these two cap-binding proteins do not share a common ancestor. In addition, structure/sequence comparisons between eIF4E and components of the nuclear cap-binding protein complex involved in pre-mRNA splicing (reviewed in Izaurralde et al., *Cell,* 78:657–668 (1994)] do not reveal any similarity.

Sequence Comparison of eIF4E: FIG. 1 documents that 66% of eIF4E's C-terminal 182 residues are highly conserved. Without exception, all 61 sites at which a significant number of differences occur map either to the surface of eIF4E(28–217). where mutations are tolerated, or represent conservative changes of buried residues unlikely to destabilize the hydrophobic core. Insertions and deletions in the nine published eIF4E sequences aligned in FIG. 1 map to random coil portions of the structure of eIF4E(28–217), where they would not disrupt α or β secondary structural elements. The remarkable level of sequence identity and the pattern of amino acid differences across phylogeny allow the conclusion to be made that all known eIF4Es share the same three-dimensional structure in their conserved C-terminal region [Sander and Schneider, *Proteins Struc. Funct. Genet.,* 9:56–68 (1991)]. Subsequent discussions of functional studies make no distinction between different eIF4Es (murine eIF4E sequence numbers are used throughout, see FIG. 1 for conversions to other sequence numbering schemes). The results of site-directed mutagenesis with various eIF4Es are consistent with the structure. Substitution of each of the five conserved, buried tryptophan residues (43, 46, 113, 130, and 166) with leucine abolished or drastically reduced cap binding [Morino et al., 1996, supra]. Less severe effects on cap binding were observed with replacement of either Trp46 or Trp130 with phenylalanine [Altmann et al., 1988, supra]. Reductions in cap-binding affinity were also obtained with Gly 111->Asp [Altmann and Trachsel, 1989, supra] and His200->Ala [Morino et al., 1996, supra], which would both destabilize the hydrophobic core.

The first 27 amino acids of murine eIF4E were omitted from the crystallization sample. In one half of the asymmetric unit, residues 28 to 35 are not visible in the electron density maps and are almost certainly disordered in one of the crystal's solvent channels. The results of the mass spectrometry/proteolysis study (FIG. 2A), suggest that the first 35 amino acids of murine eIF4E are disordered in the absence of other proteins. In the other half of the asymmetric unit, residues 28 to 35 are stabilized by lattice packing interactions that are probably unique to this particular crystalline state of truncated eIF4F.

Figure 4A:
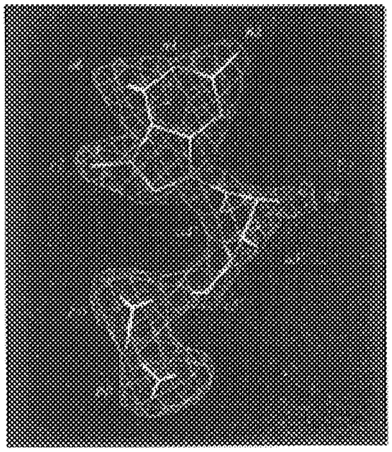
FIG. 4A is a ($2|F_{observed}|-|F_{calculated}|$) simulated annealing omit map [Br ünger, X-PLOR v. 3.1 manual, New Haven: Yale University (1993B)] showing 7-methyl-GDP, calculated at 2.2 Å resolution with the ligand omitted from the phasing model. The contour level is 1.3σ_and the refined atomic model is shown as a color-coded stick figure. There is no significant electron density for O3', which is consistent with the ribose ring being conformationally flexible in the complex. The view of the ligand is identical to those shown in FIGS. 3B and 4B.
Figure 4B:
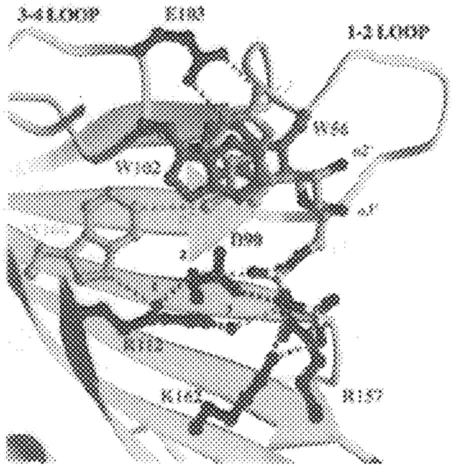
FIG. 4B is a RIBBONS drawing of 7-methyl-GDP in the cap-binding slot of eIF4E, showing selected residues involved in cap-analogue recognition. Hydrogen bonds, van der Waals interactions and salt-bridges are indicated with dotted lines. The three bridging water molecules are shown as black spheres, labeled 1, 2, and 3. This view is identical to that shown in FIG. 3B.
Figure 4C:
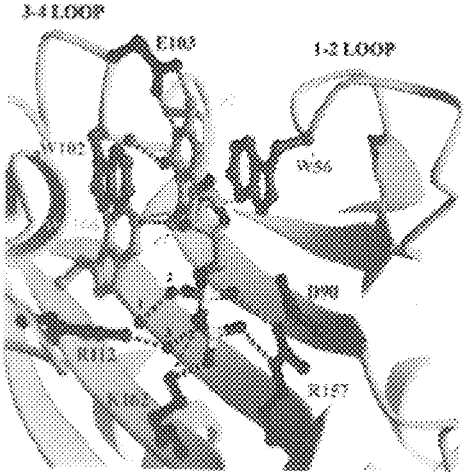
FIG. 4C is a RIBBONS drawing of 7-methyl-GDP in the cap-binding slot. This view is identical to that shown in FIG. 3A, and perpendicular to the view in FIG. 4B.

Structure of eIF4E-bound 7-methyl-GDP: FIG. 4 illustrates the structure of eIF4E-bound 7-methyl-GDP (for clarity all 7-methyl-GDP atom names appear in italics in the text and in italics and lower case in the labeling of FIGS. 4A–C). The electron density for the cap homologue is well-defined in both protein-ligand complexes (FIG. 4A), and the two crystallographically-independent copies of 7-methyl-GDP are similar (r.m.s. deviation between equivalent atoms=0.4 Å). The ligand is bound to eIF4E in an extended conformation with an anti-glycosyl C1'-N linkage (χ=−160°) and a C4'-exo ribose pucker (pseudorotation angle=53°). The orientation about the C4'-C5' bond is gauche,gauche (O5'-C5'-C4'-O4' torsion angle=−78°; O5'-C5'-C4'-C3' torsion angle=35°). The two phosphate groups (α and β) also adopt an extended conformation. This ligand conformation is similar to that observed for 7-methyl-GMP interacting with L-Trp-L-Clu [Ishida et al., *J. Chem. Soc. Perkin Trans.,*

I:1847–1853 (1991)]. The only significant difference between the two nucleotide structures is the ribose pucker, which is C3'-exo in the complex with L-Trp-L-Glu. This difference can be readily explained in terms of ribose torsion angle flexibility, because there is only one protein-ligand interaction involving the ribose group (see below).

7-methyl-GDP Binding:

The structure of the murine eIF4E(28–217)-7-methyl-GDP complex represents the first example of a protein bound to an alkylated base [for reviews of protein-DNA and protein-RNA complex structures see Patikoglou and Burley, *Ann. Rev. Biophys. Biomolec. Struct.,* 26:287–323 (1997); Nagai, *Curr. Opin. Struct. Biol.,* 6:53–61 (1996)]. 7-methyl-GDP contacts are completely restricted to the basal surface of eIF4E(28–217), where the cap homologue lies in the cap-binding slot (FIGS. 3A–C). Although their crystal lattice environments are not the same, the two crystallographically-independent eIF4E-nucleotide complexes make essentially identical protein-ligand interactions, burying portions of both the protein and 7-methyl-GDP surfaces (total buried surface area/eIF4E-7-methyl-GDP complex=610 Å$^2$). Electron density features corresponding to nine well-ordered water molecules were found within each protein-ligand interface. These trapped waters are common to both complexes, creating similar hydrogen-bonded networks of water molecules bridging the gap between the protein and the ribose and phosphate groups (see below).

The alkylated base interacts primarily with the S1-S2 and S3-S4 loops (see below), where it is sandwiched between the sidechains of two conserved tryptophans (Trp56 and Trp102). This mode of sidechain-base interaction is consistent with the results of small molecule crystallographic work on model systems [Ishida et al., *Biochemistry,* 22:3571–3581 (1983); Ishida et al., *J. Amer. Chem. Soc.,* 110:2286–2294 (1988); Ishida et al., 1991, supra], and fluorescence studies with eIF4E [Ueda et al., *J. Biochem.,* 109:882–889 (1992A)]. It can be explained in terms of enhancement of π-π stacking enthalpy, because of charge transfer between the electron deficient 7-methyl-guanine (which carries a delocalized positive charge secondary to methylation) and the electron rich indole groups [for a detailed quantum mechanical analysis of the energetics of stacking interactions between indole and 7-methyl-guanine see Ishida et al., 1988, supra]. Not surprising, Trp56->Leu and Trp102->Leu abolished cap binding [Ueda et al., *EBS Letts.,* 280:207–210 (1991); Morino et al., 1996, supra]. Whereas, substitutions that preserve the sidechain π-electron cloud (Trp56->Phe and Trp102->Phe) only reduce cap-binding activity by 50% or more [Altmann et al., 1988, supra].

The N7 methyl group and O6 are oriented towards the floor of the cap-binding slot, where O6 makes a hydrogen bond with the backbone amino group of Trp102. N1 and N2 emerge from between the two tryptophan sidechains, where they make hydrogen bonds with the carboxylate oxygen atoms of Glu103 (see below). Substitution of this residue with Ala also abolishes cap binding [Morino et al., 1996, supra]. Thus, eIF4E serves as a receptor for 7-methyl-guanine by satisfying the hydrogen bonding requirements for Watson-Crick base pairing provided by cytidine (a donor plus two acceptors). The N7-methyl group makes a van der Waals contact with the sidechain of Trp166 (see below). That both π-π stacking and similar hydrogen bonding interactions were observed between 7-methyl-GMP and L-Trp-L-Glu using small-molecule crystallography [Ishida et al., 1991, supra] is also seen with the present protein-ligand crystal analysis was completely unexpected.

The ribose and disphosphate moieties extend away from the methylated purine towards the entrance to the cap-binding slot, terminating shortly before the end of the β-sheet (FIGS. 3A, 4B–C). The plane of the ribose group lies almost perpendicular to the plane of the alkylated base with its O2' and O3' hydroxyl groups directed out to the solvent, and O4' pointing towards Trp56. The positions of the ribose and phosphate groups are stabilized by salt bridges and water-mediated hydrogen bonds.

Inter-atomic contacts between eIF4E(28–217) and 7-methyl-GDP can be divided into four classes (FIGS. 4B–C). (1) Sandwiching of the alkylated base between Trp56 and Trp102 (interplanar distances=3.5–3.6 Å). (2) Residues making hydrogen bonds or van der Waals contacts with 7-methyl-guanine include Trp102 (N—O6=2.7 Å), Glu103 (OE1—N1=2.9 Å; OE2—N2=2.7 Å), and Trp166 (CH2—C7=3.7 Å). (3) Direct interactions between the ribose and diphosphate moieties and the protein include, Trp56 and the ribose group (CG—C1'=3.7 Å), Arg157 and α- and β-phosphate oxygen atoms (NH2—PαO1=3.0 Å; NE—PβO1=3.1 Å), and Lys162 and α- and β-phosphate oxygen atoms (NZ—PαO3=3.1 Å; NZ—PβO2=2.9 Å). The position of Argl57 is stabilized by a salt bridge with Asp90 (OD1—NH2=2.8 Å). (4) Two residues projecting from the floor of the cap-binding slot make water-mediated contacts with 7-methyl-GDP via three of the nine water molecules trapped between the ligand and the protein. These three bridging waters are found in virtually the same relative positions in the two crystallographically-independent complexes comprising the asymmetric unit. Trp166 plus two water molecules interacts with one of the α-phosphate oxygen atoms (NE1—H2O1=3.0 Å; H2O1—H2O2=2.8 Å; H2O2ÅPαO2=3.1 Å). Arg112 plus another water molecule interacts with the oxygen atom that provides the ester linkage between the two phosphorous atoms (NZ—H2O3=2.4 Å; H2O3—PαO3=3.2 Å). O4' is oriented toward the walls of the cap-binding slot, and O2', O3', O5' and PβO3 are solvent accessible and appear to make hydrogen bonds with water molecules in the first shell of hydration.

Earlier work demonstrating a pH optimum of 7.6 for mRNA cap binding/translation and measurement of a pKa of 7.4 for the N1 proton of 7-methyl-GTP in translation buffer [Rhoads et al., *Biochemistry,* 22:6084–6088 (1983)], lead to suggestions that the enolate form of 7-methyl-guanine (in which N1 is deprotonated) may be recognized by eIF4E. The cocrystal structure shows conclusively that eIF4E recognizes the keto form of 7-methyl-GDP, because the N1 proton is required for hydrogen bond donation to Glu103. Presumably, the chemical microenvironment provided by the negative charge of Glu103 increases the pKa of the N1 proton in its eIF4E-bound state.

Finally, the structure of the protein-7-methyl-GDP complex explains why guanine, GMP, GDP, and GTP do not competitively inhibit translation initiation. Unlike eIF4E, the GTP-binding proteins (Ras p21, EF-Tu, ARF1 and the heterotrimeric G-proteins) share a core domain, consisting of five α-helices and a 6-stranded β-sheet [reviewed in Kjeldgaard et al., *FASEB J.,* 10:1347–1368 (1996)]. Interactions between GTP-binding proteins and guanine do include hydrogen bonds between O6 and a backbone amino group, and between N1 and N2 and a conserved acidic residue. However, they cannot bind 7-methyl-guanine because N7 is used as a hydrogen bond acceptor in complexes with GTP-binding proteins. (The N7 methyl group makes van der Waals contact with Trp166 of eIF4E). The hydrophobic GTP-binding cleft also differs from the cap-binding slot, and this finding may explain why eIF4E requires guanine alkylation to form a tight protein-ligand complex. GTP-binding proteins sandwich guanine between various aliphatic sidechains, but none of these residues are capable of π-π stacking with a positively-charged alkylated base.

Implications for mRNA 5' Cap Recognition: This work provides the first high resolution view of a protein recognizing a mRNA 5' cap analogue. More important, the murine eIF4E(28–217)-7-methyl-GDP cocrystal structure reveals protein-ligand interactions that are entirely compatible with the primary sequences of all known eIF4Es. Without exception, the four residues making contacts with 7-methyl-guanine (Trp56, Trp102, Glu103, Trp166) are absolutely conserved among all published eIF4E sequences (FIG. 1). Of the three residues that interact with the two phosphate groups, Arg157 is absolutely conserved. The same is true of Asp90, which stabilizes the position of Arg157 via a salt bridge. The remaining two residues (Arg112, Lys162) make either direct or water-mediated contacts with phosphates, and are either arginine or lysine in the sequences listed in FIG. 1. Thus, the mode of 7-methyl-GDP binding observed in our cocrystal structure is common to all known eIF4Es.

The eIF4E-7-methyl-GDP cocrystal structure of the present invention is also compatible with the results of all published binding studies carried out with cap analogues or mRNAs bearing modified 5' caps. Although N7-methylation of guanine is essential for cap recognition in vivo [GMP, GDP, and GTP are ineffective competitors, see Darzynkiewicz et al., *Biochemistry,* 24:1701–1707 (1985)], a variety of N7substituents support eIF4E binding in vitro [Darzynkiewicz et al., *Biochemistry,* 28:4771–4778 (1989)]. Substitution of the methyl group at N7 with either ethyl, benzyl or 2-phenylethyl yields cap analogues that inhibit cap-dependent translation initiation. Conversely, propyl, isopropyl, butyl, isobutyl, cyclopentyl, carboxymethyl, and 1-phenylethyl substituents have no effect on translation. Furthermore, mRNA caps modified at N7 with either benzyl or ethyl groups support translation in vitro [Furuichi et al., *J. Biol. Chem.,* 254:6732–6738 (1979); Darzynkiewicz et al., 1989, supra]. Model building studies with the present structure indicate that ethyl, benzyl or 2-phenylethyl moieties can fit in the water-filled cavity found between 7-methyl-GDP and eIF4E. These predictions are supported by earlier findings that 7-benzyl-G capped mRNA is translated at almost twice the level of normally-capped mRNA [Darzynkiewicz et al., 1989, supra], which can be explained in terms of extrusion of additional water molecules from the protein-ligand interface giving a higher entropy change on binding and hence a higher affinity for eIF4E.

Modifications that abolish or reduce eIF4E binding include: substitution of O6 with a chlorine atom [Adams et al., *J. Biol. Chem.,* 253:2589–2595 (1978)], precluding the Trp102—O6 hydrogen bond; methylation of the N1 position of 7-methyl-GDP [Adams et al., 1978, supra], eliminating the Glu103—N1 hydrogen bond; double methylation of N2 [Darzynkiewicz et al., *Nucl. Acids Res.,* 16:8953–8962 (1988)] or removal of N2 giving 7-methyl-inosine [Adams et al., 1978, supra; Ueda et al., 1992A, supra], preventing formation of the Glu103-N2 hydrogen bond; reduction of 7-methyl-GDP to 8-hydro-7-methyl-GDP [Adams et al., 1978, supra], which would reduce the delocalized positive charge on the alkylated base. Substitutions that affect solvent accessible portions of 7-methyl-GDP and have little or no effect on cap binding and/or translation include: single methylation of N2 [Darzynkiewicz et al., 1988, supra]; O2'- or O3'-methylation [Darzynkiewicz et al., 1985, supra]; removal of the 2' hydroxyl group [-Darzynkiewicz et al., 1985, supra]; and methylation of the β- or γ-phosphate groups [Darzynkiewicz et al., 1985, supra].

Figure 5A:
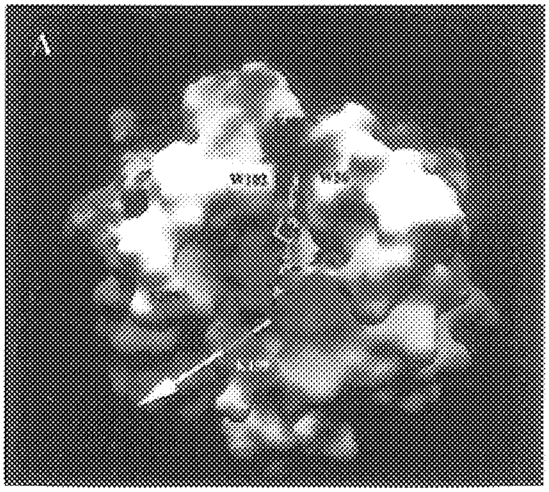
FIG. 5A depicts the cap-binding surface of eIF4E, showing 7-methyl-GDP in the cap-binding slot. The surface is color coded for electrostatic potential and labeled with the locations of selected residues involved in cap-analogue recognition (Trp56, TrpIO2 and Glu103). This view is identical to that shown in FIG. 3A. The putative path of an mRNA ligand is indicated with a yellow arrow, which is shown passing between Ser209 and Lys159.

The eIF4E-7-methyl-GDP cocrystal structure is also consistent with the well-established finding that mRNA binding is not affected by the identity of the base following the cap [reviewed in Shatkin, 1976, supra]. The electrostatic potential surface of the cap-binding slot, illustrated in FIG. 5A, reveals that the binding surface can be divided into three portions. At the slot's deepest point, the presence of Glu103 is responsible for the calculated negative electrostatic potential (denoted in red), which would partially neutralize the positive charge on the alkylated base. Where the ribose moiety binds in the middle of the slot, the calculated electrostatic potential is neutral (denoted in white), because of the hydrophobic character of Trp56, Trp102 and Trp166. At the entrance to the slot, Arg112, Arg157, and Lys162 generate the calculated positive electrostatic potential (denoted in blue), which partially neutralizes the two phosphate groups of 7-methyl-GDP. FIG. 5A shows that the positively-charged slot extends beyond the limits of the ligand used in this work, suggesting a chemically-reasonable binding site for the γ-phosphate groups of 7-methyl-GTP or 7-methyl-G(5')ppp(5')N. (see FIG. 5A for a hypothetical path for the mRNA).

Figure 5B:
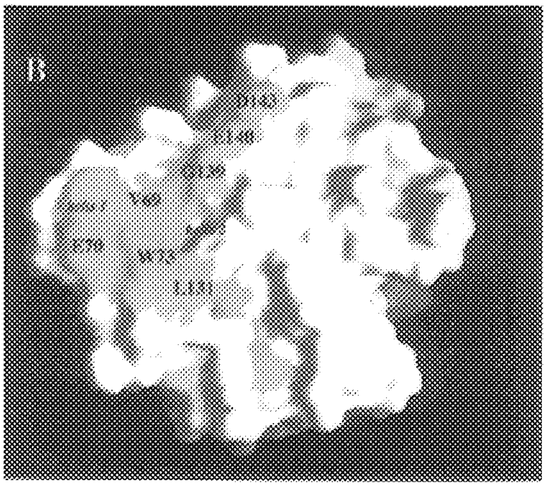
FIG. 5B depicts the convex dorsal surface of eIF4E, showing green color-coded locations of surface accessible residues that are absolutely conserved among all nine known sequences of eIF4E (see FIG. 1). This view is identical to that shown in FIG. 3D.
Figure 5C:
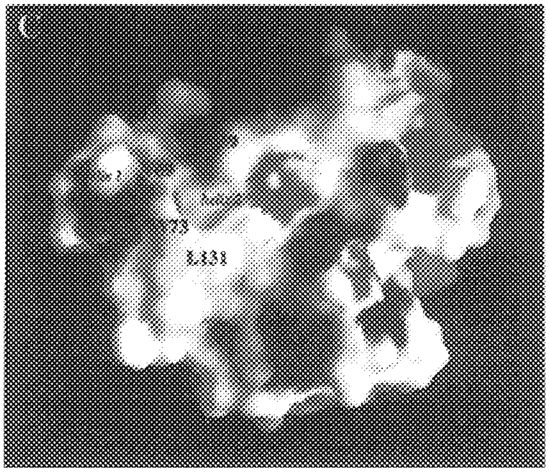
FIG. 5C depicts the solvent-accessible surface of the convex face of eIF4E, color coded for electrostatic potential and labeled with the locations of absolutely conserved solvent-accessible residues. This view are identical to those shown in FIGS. 3D and 5B.

FIG. 5A also illustrates the location of Ser209, which is phosphorylated in response to treatment of cells with growth factors, hormones and mitogens [reviewed in Sonenberg, 1996, supra]. Although the present cocrystal structure does not include either a phosphate group at Ser209 or 7-methyl-G(5')ppp(5')N, the structure does provide sufficient information with which to deduce a model for the stimulatory effects of Ser209 phosphorylation. At the current stage of crystallographic refinement, a well-localized electron density for the sidechain of Lys159 is not available. However, model building demonstrates that this apparently flexible sidechain could adopt a conformation that would bring its positively-charged amino group to within 7.5 Å of the hydroxyl group of Ser209. In addition, electron density for the 114-S8 loop is only seen in one of the two eIF4E-7-methyl-GDP complexes comprising the asymmetric unit (see Experimental Procedures), suggesting that this portion of the polypeptide chain is relatively flexible. Therefore, phosphorylation of Ser209 should generate a salt bridge with Lys159, which would introduce a retractable bridge covering the cap-binding slot near its entrance (FIG. 5A). Phosphorylated Ser209 and Lys159 might together act as a clamp, which would help stabilize the mRNA in the cap-binding slot. A similar effect has been observed in carboxypeptidase A, where Tyr248 acts as a retractable cover for ligands bound in the active-site cleft [reviewed in Christianson and Lipscomb, *Acc. Chem. Res.,* 22:62–69 (1988)]. The proposed model of mRNA-binding stabilization following phosphorylation is consistent with an earlier report that phosphorylated eIF4E exhibits a 3–4 fold increase in 7-methyl-GTP binding activity, compared with its non-phosphorylated form [Minich et al., *Proc. Natl. Acad. Sci. USA,* 91:7668–7672 (1994)]. This enhanced inter-molecular interaction underscores the importance of regulation of eIF4E activity by phosphorylation under conditions of growth stimulation.

eIF4E-Translation Factor Interactions:

The cocrystal structure of eIF4E also provides a basis for analyzing contacts between eIF4E and proteins that interact with eIF4E during translation initiation. FIGS. 3D and 5B–C illustrate the convex dorsal surface of eIF4E, where α-helices H1 and H2 display solvent-accessible, hydrophobic and acidic residues that are phylogenetically-conserved.

The green color-coded portion of the molecular surface depicted in FIG. 5B corresponds to surface-accessible residues that are absolutely conserved among all nine known eIF4Es (FIG. 1). Val69, Trp73, Leu131 and Gly139 contribute to the non-polar part of this surface (white in FIG. 5C), and Glu7O, Glu14 and Asp143 contribute to its acidic portion (red in FIG. 5C). This conserved surface feature may be important for interactions with eIF4G and with the 4E-binding proteins, which share a Tyr-X-X-X-X-Leu-Leu motif in which X is any amino acid and the second leucine is not strictly invariant [Mader et al., 1995, supra; Altmann et al., 1997, supra]. Preincubation of eIF4E with eIF4G precludes binding of 4E-BP1 and vice-versa [Haghighat et al., 1995, supra], suggesting that the conserved hydrophobic surface feature on the concave dorsal surface of eIF4E could be a common binding site for the sequence Tyr-X-X-X-X-Leu-Leu. The conserved acidic residues (Glu70, Glu140 and Asp143) might be responsible for destabilizing complexes between eIF4E and phosphorylated 4E-BPs via electrostatic repulsion.

Novel RNA-Binding Fold and Mechanism: Comparison of our structure of the eIF4E-7 -methyl-GDP complex with the three-dimensional structures of other RNA-binding proteins demonstrates that eIF4E represents a novel RNA-binding fold. Excluding the transfer RNA synthetases and the E. coli Rop protein, all known RNA-binding motifs are α/β proteins in which a β-sheet is packed against a pair of α-helices [reviewed in Nagai, 1996, supra]. The present census of RNA-protein complexes includes, the RNA bacteriophage MS2 coat protein interacting with a 19-nucleotide hairpin [Valegard et al., *Nature,* 371:623–626 (1994)], and the RNA-binding domain of the UA1 spliceosomal protein complexed with a 21-nucleotide hairpin [Oubridge et al., *Nature,* 372:432–438 (1994)]. Although MS2, U1 and eIF4E are all α/β-proteins, the RNA-binding surfaces of MS2 and U1 are large, relatively flat β-sheets to which the stem and loop of the hairpin are approximated. In contrast, the "RNA-binding site" in eIF4E is a narrow slot that interacts with a single-stranded nucleic acid ligand.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A crystal of a protein-ligand complex comprising a protein-ligand complex of an N-terminal truncated eIF4E and a ligand, wherein the crystal effectively diffracts X-rays for the determination of the atomic coordinates of the protein-ligand complex to a resolution of greater than 5.0 Angstroms; and wherein the N-terminal truncated eIF4E:

(a) lacks at least ten amino acids from the flexible N-terminus of the corresponding full-length eIF4E; and (b) retains the globular core of the corresponding full-length eIF4E.

2. The crystal of claim 1, wherein the ligand comprises an alkylated base.

3. The crystal of claim 2, wherein the N-terminal truncated eIF4E has an amino acid sequence of amino acids 28 to 217 of SEQ ID NO:1, or an amino acid sequence that differs from amino acid 28 to 217 of SEQ ID NO:1 by only having conservative substitutions.

4. The crystal of claim 3, wherein the ligand is 7-methyl guanosine diphosphate.

5. The crystal of claim 4 having space group of $P2_12_12_1$ and a unit cell of dimensions of a=59.3, b=74.8 and c=76.3.

6. The crystal of claim 4 wherein the N-terminal truncated eIF4E has secondary structural elements that include three long α-helices, one short α-helix, and an eight-stranded, antiparallel β-sheet, arranged in the order: β-Sheet(1), β-Sheet(2), α-Helix(1), β-Sheet(3), β-Sheet(4), α-Helix(2), β-Sheet(5), β-Sheet(6), α-Helix(3), β-Sheet(7), α-Helix(4), β-Sheet(8).

7. An N-terminal truncated vertebrate eIF4E lacking 20 to 40 of the first forty N-terminal amino acids of the corresponding full-length eIF4E.

8. The N-terminal truncated eIF4E of claim 7 having an amino acid sequence of amino acids 28 to 217 of SEQ ID NO:1 or an amino acid sequence that differs from amino acid 28 to 217 of SEQ ID NO:1 by only having conservative substitutions.

9. The N-terminal truncated eIF4E of claim 8 comprising a selenomethionine that has been substituted for a methionine in said amino acid sequence.

10. The N-terminal truncated eIF4E of claim 7 having an amino acid sequence of amino acids 33 to 217 of SEQ ID NO:1 or an amino acid sequence that differs from amino acid 33 to 217 of SEQ ID NO:1 by only having conservative substitutions.

11. A method of using the crystal of claim 1 in a drug screening assay comprising:

(a) selecting a potential ligand by performing rational drug design with the three-dimensional structure determined for the crystal, wherein said selecting is performed in conjunction with computer modeling;

(b) contacting the potential ligand with the ligand binding domain of eIF4E; and (c) detecting the binding of the potential ligand for the ligand binding domain; wherein a potential drug is selected on the basis of its having a greater affinity for the ligand binding domain of eIF4E than that of a standard ligand for the ligand binding domain of eIF4E.

12. The method of claim 11 wherein the standard ligand in step (b) is 7-methyl guanosine diphosphate.

13. The method of claim 11 further comprising:

(d) growing a supplemental crystal containing a protein-ligand complex formed between the N-terminal truncated eIF4E and the potential drug, wherein the crystal effectively diffracts X-rays for the determination of the atomic coordinates of the protein-ligand complex to a resolution of greater than 5.0 Angstroms;

(e) determining the three-dimensional structure of the supplemental crystal with molecular replacement analysis;

(f) selecting a candidate drug by performing a rational drug design with the three-dimensional structure determined for the supplemental crystal, wherein said selecting is performed in conjunction with computer modeling;

(g) contacting the candidate drug with a cell that expresses eIF4E; and (h) detecting a measure of protein synthesis in the cell; wherein a candidate drug is identified as a drug when it inhibits the measure of protein synthesis in the cell.

14. The method of claim 13 further comprising an initial step that precedes step (a) wherein said initial step consists of determining the three-dimensional structure of a crystal comprising a protein-ligand complex formed between an N-terminal truncated eIF4E and 7-methyl guanosine diphosphate, wherein the crystal effectively diffracts X-rays for the determination of the atomic coordinates of the protein-ligand complex to a resolution of greater than 5.0 Angstroms.

15. A method of using the crystal of claim 1 in a drug screening assay comprising:

(a) selecting a potential antagonist by performing rational drug design with the three-dimensional structure determined for the crystal, wherein said selecting is performed in conjunction with computer modeling;

(b) adding the potential antagonist to a protein synthesis assay in which the eIF4E is a rate-limiting factor; and (c) detecting a measure of protein synthesis; wherein a potential agonist that inhibits the measure of protein synthesis is selected as a potential drug.

16. The method of claim 15 wherein said protein synthesis assay is an in vitro protein synthesis assay.

17. The method of claim 15 further comprising:

(d) growing a supplemental crystal comprising a protein-ligand complex formed between the N-terminal truncated eIF4E and the potential drug, wherein the crystal effectively diffracts X-rays for the determination of the atomic coordinates of the protein-ligand complex to a resolution of greater than 5.0 Angstroms;

(e) determining the three-dimensional structure of the supplemental crystal with molecular replacement analysis;

(f) selecting a candidate drug by performing a rational drug design with the three-dimensional structure determined for the supplemental crystal, wherein said selecting is performed in conjunction with computer modeling;

(g) contacting the candidate drug with a cell that expresses eIF4E; and (h) detecting a measure of protein synthesis in the cell; wherein a candidate drug is identified as a drug when it inhibits the measure of protein synthesis in the cell.

18. The method of claim 17 further comprising an initial step that precedes step (a) wherein said initial step consists of determining the three-dimensional structure of a crystal comprising a protein-ligand complex formed between an N-terminal truncated eIF4E and a standard ligand for eIF4E, wherein the crystal effectively diffracts X-rays for the determination of the atomic coordinates of the protein-ligand complex to a resolution of greater than 5.0 Angstroms.

19. A method of using the N-terminal truncated eIF4E of claim 1 to grow a crystal of a protein-ligand complex comprising:

(a) contacting the N-terminal truncated eIF4E with a ligand, wherein the N-terminal truncated eIF4E forms a protein-ligand complex with the ligand; and (b) growing the crystal of the protein-ligand complex; wherein the crystal effectively diffracts X-rays for the determination of the atomic coordinates of the protein-ligand complex to a resolution of greater than 5.0 Angstroms.

20. The method of claim 19 wherein said growing is performed by sitting-drop vapor diffusion.

21. The method of claim 19 wherein said ligand comprises an alkylated base.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 217 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Ala | Thr | Val | Glu | Pro | Glu | Thr | Thr | Pro | Thr | Thr | Asn | Pro | Pro | Pro |
| 1 | | | | 5 | | | | | 10 | | | | | 15 | |
| Ala | Glu | Glu | Glu | Lys | Thr | Glu | Ser | Asn | Gln | Glu | Val | Ala | Asn | Pro | Glu |
| | | | 20 | | | | | 25 | | | | | 30 | | |
| His | Tyr | Ile | Lys | His | Pro | Leu | Gln | Asn | Arg | Trp | Ala | Leu | Trp | Phe | Phe |
| | | 35 | | | | | 40 | | | | | 45 | | | |
| Lys | Asn | Asp | Lys | Ser | Lys | Thr | Trp | Gln | Ala | Asn | Leu | Arg | Leu | Ile | Ser |
| | 50 | | | | | 55 | | | | | 60 | | | | |
| Lys | Phe | Asp | Thr | Val | Glu | Asp | Phe | Trp | Ala | Leu | Tyr | Asn | His | Ile | Gln |
| 65 | | | | | 70 | | | | | 75 | | | | | 80 |
| Leu | Ser | Ser | Asn | Leu | Met | Pro | Gly | Cys | Asp | Tyr | Ser | Leu | Phe | Lys | Asp |
| | | | | 85 | | | | | 90 | | | | | 95 | |
| Gly | Ile | Glu | Pro | Met | Trp | Glu | Asp | Glu | Lys | Asn | Lys | Arg | Gly | Gly | Arg |
| | | | 100 | | | | | 105 | | | | | 110 | | |
| Trp | Leu | Ile | Thr | Leu | Asn | Lys | Gln | Gln | Arg | Arg | Ser | Asp | Leu | Asp | Arg |
| | | 115 | | | | | 120 | | | | | 125 | | | |
| Phe | Trp | Leu | Glu | Thr | Leu | Leu | Cys | Leu | Ile | Gly | Glu | Ser | Phe | Asp | Asp |

130 135 140

Tyr Ser Asp Asp Val Cys Gly Ala Val Val Asn Val Arg Ala Lys Gly
145 150 155 160

Asp Lys Ile Ala Ile Trp Thr Thr Glu Cys Glu Asn Arg Asp Ala Val
165 170 175

Thr His Ile Gly Arg Val Tyr Lys Glu Arg Leu Gly Leu Pro Pro Lys
180 185 190

Ile Val Ile Gly Tyr Gln Ser His Ala Asp Thr Ala Thr Lys Ser Gly
195 200 205

Ser Thr Thr Lys Asn Arg Phe Val Val
210 215

( 2 ) INFORMATION FOR SEQ ID NO:2:

( i ) SEQUENCE CHARACTERISTICS:
( A ) LENGTH: 217 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:2:

Met Ala Thr Val Glu Pro Glu Thr Thr Pro Thr Pro Asn Pro Pro Thr
1 5 10 15

Thr Glu Glu Glu Lys Thr Glu Ser Asn Gln Glu Val Ala Asn Pro Glu
20 25 30

His Tyr Ile Lys His Pro Leu Gln Asn Arg Trp Ala Leu Trp Phe Phe
35 40 45

Lys Asn Asp Lys Ser Lys Thr Trp Gln Ala Asn Leu Arg Leu Ile Ser
50 55 60

Lys Phe Asp Thr Val Glu Asp Phe Trp Ala Leu Tyr Asn His Ile Gln
65 70 75 80

Leu Ser Ser Asn Leu Met Pro Gly Cys Asp Tyr Ser Leu Phe Lys Asp
85 90 95

Gly Ile Glu Pro Met Trp Glu Asp Glu Lys Asn Lys Arg Gly Gly Arg
100 105 110

Trp Leu Ile Thr Leu Asn Lys Gln Gln Arg Arg Ser Asp Leu Asp Arg
115 120 125

Phe Trp Leu Glu Thr Leu Leu Cys Leu Ile Gly Glu Ser Phe Asp Asp
130 135 140

Tyr Ser Asp Asp Val Cys Gly Ala Val Val Asn Val Arg Ala Lys Gly
145 150 155 160

Asp Lys Ile Ala Ile Trp Thr Thr Glu Cys Glu Asn Arg Glu Ala Val
165 170 175

Thr His Ile Gly Arg Val Tyr Lys Glu Arg Leu Gly Leu Pro Pro Lys
180 185 190

Ile Val Ile Gly Tyr Gln Ser His Ala Asp Thr Ala Thr Lys Ser Gly
195 200 205

Ser Thr Thr Lys Asn Arg Phe Val Val
210 215

( 2 ) INFORMATION FOR SEQ ID NO:3:

( i ) SEQUENCE CHARACTERISTICS:
( A ) LENGTH: 217 amino acids
( B ) TYPE: amino acid (C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:3:

```
Met Ala Thr Val Glu Pro Glu Thr Thr Pro Thr Thr Asn Pro Pro Pro
1               5                   10                  15

Ala Glu Glu Glu Lys Thr Glu Ser Asn Gln Glu Val Ala Asn Pro Glu
            20                  25                  30

His Tyr Ile Lys His Pro Leu Gln Asn Arg Trp Ala Leu Trp Phe Phe
        35                  40                  45

Lys Asn Asp Lys Ser Lys Thr Trp Gln Ala Asn Leu Arg Leu Ile Ser
    50                  55                  60

Lys Phe Asp Thr Val Glu Asp Phe Trp Ala Leu Tyr Asn His Ile Gln
65                  70                  75                  80

Leu Ser Ser Asn Leu Met Pro Gly Cys Asp Tyr Ser Leu Phe Lys Asp
                85                  90                  95

Gly Ile Glu Pro Met Trp Glu Asp Glu Lys Asn Lys Arg Gly Gly Arg
            100                 105                 110

Trp Leu Ile Thr Leu Asn Lys Gln Gln Arg Arg Ser Asp Leu Asp Arg
        115                 120                 125

Phe Trp Leu Glu Thr Leu Leu Cys Leu Ile Gly Glu Ser Phe Asp Asp
    130                 135                 140

Tyr Ser Asp Asp Val Cys Gly Ala Val Val Asn Val Arg Ala Lys Gly
145                 150                 155                 160

Asp Lys Ile Ala Ile Trp Thr Thr Glu Cys Glu Asn Arg Asp Ala Val
                165                 170                 175

Thr His Ile Gly Arg Val Tyr Lys Glu Arg Leu Gly Leu Pro Pro Lys
            180                 185                 190

Ile Val Ile Gly Tyr Gln Ser His Ala Asp Thr Ala Thr Lys Ser Gly
        195                 200                 205

Ser Thr Thr Lys Asn Arg Phe Val Val
    210                 215
```

(2) INFORMATION FOR SEQ ID NO:4:

(i) SEQUENCE CHARACTERISTICS:
(A) LENGTH: 217 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:4:

```
Met Ala Thr Val Glu Pro Glu Thr Thr Pro Thr Pro Asn Pro Pro Pro
1               5                   10                  15

Ala Glu Glu Glu Lys Thr Glu Ser Asn Gln Glu Val Ala Asn Pro Glu
            20                  25                  30

His Tyr Ile Lys His Pro Leu Gln Asn Arg Trp Ala Leu Trp Phe Phe
        35                  40                  45

Lys Asn Asp Lys Ser Lys Thr Trp Gln Ala Asn Leu Arg Leu Ile Ser
    50                  55                  60

Lys Phe Asp Thr Val Glu Asp Phe Trp Ala Leu Tyr Asn His Ile Gln
65                  70                  75                  80
```

Leu Ser Ser Asn Leu Met Pro Gly Cys Asp Tyr Ser Leu Phe Lys Asp
85 90 95

Gly Ile Glu Pro Met Trp Glu Asp Glu Lys Asn Lys Arg Gly Gly Arg
100 105 110

Trp Leu Ile Thr Leu Asn Lys Gln Gln Arg Arg Ser Asp Leu Asp Arg
115 120 125

Phe Trp Leu Glu Thr Leu Leu Cys Leu Ile Gly Glu Ser Phe Asp Asp
130 135 140

Tyr Ser Asp Asp Val Cys Gly Ala Val Val Asn Val Arg Ala Lys Gly
145 150 155 160

Asp Lys Ile Ala Ile Trp Thr Thr Glu Cys Glu Asn Arg Asp Ala Val
165 170 175

Thr His Ile Gly Arg Val Tyr Lys Glu Arg Leu Gly Leu Pro Pro Lys
180 185 190

Ile Val Ile Gly Tyr Gln Ser His Ala Asp Thr Ala Thr Lys Ser Gly
195 200 205

Ser Thr Thr Lys Asn Arg Phe Val Val
210 215

( 2 ) INFORMATION FOR SEQ ID NO:5:

( i ) SEQUENCE CHARACTERISTICS:
( A ) LENGTH: 213 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:5:

Met Ala Ala Val Glu Pro Glu Asn Thr Asn Pro Gln Ser Thr Glu Glu
1 5 10 15

Glu Lys Glu Thr Gly Gln Glu Ile Val Ser Pro Asp Gln Tyr Ile Lys
20 25 30

His Pro Leu Gln Asn Arg Trp Ala Leu Trp Phe Phe Lys Asn Asp Lys
35 40 45

Ser Lys Thr Trp Gln Ala Asn Leu Arg Leu Ile Ser Lys Phe Asp Thr
50 55 60

Val Glu Asp Phe Trp Ala Leu Tyr Asn His Ile Gln Leu Ser Ser Asn
65 70 75 80

Leu Met Ser Gly Cys Asp Tyr Ser Leu Phe Lys Asp Gly Ile Glu Pro
85 90 95

Met Trp Glu Asp Glu Lys Asn Lys Arg Gly Gly Arg Trp Leu Ile Thr
100 105 110

Leu Asn Lys Gln Gln Arg Arg Asn Asp Leu Asp Arg Phe Trp Leu Glu
115 120 125

Thr Leu Met Cys Leu Ile Gly Glu Ser Phe Asp Glu His Ser Asp Asp
130 135 140

Val Cys Gly Ala Val Val Asn Val Arg Ala Lys Gly Asp Lys Ile Ala
145 150 155 160

Ile Trp Thr Thr Glu Phe Glu Asn Lys Asp Ala Val Thr His Ile Gly
165 170 175

Arg Val Tyr Lys Glu Arg Leu Gly Leu Pro Ala Lys Val Val Ile Gly
180 185 190

Tyr Gln Ser His Ala Asp Thr Ala Thr Lys Ser Gly Ser Thr Thr Lys 195 200 205

Asn Arg Phe Val Val
210

( 2 ) INFORMATION FOR SEQ ID NO:6:

( i ) SEQUENCE CHARACTERISTICS:
( A ) LENGTH: 259 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:6:

Met Gln Ser Asp Phe His Arg Met Lys Asn Phe Ala Asn Pro Lys Ser
1 5 10 15

Met Phe Lys Thr Ser Ala Pro Ser Thr Glu Gln Gly Arg Pro Glu Pro
20 25 30

Pro Thr Ser Ala Ala Ala Pro Ala Glu Ala Lys Asp Val Lys Pro Lys
35 40 45

Glu Asp Pro Gln Glu Thr Gly Glu Pro Ala Gly Asn Thr Ala Thr Thr
50 55 60

Thr Ala Pro Ala Gly Asp Asp Ala Val Arg Thr Glu His Leu Tyr Lys
65 70 75 80

His Pro Leu Met Asn Val Trp Thr Leu Trp Tyr Leu Glu Asn Asp Arg
85 90 95

Ser Lys Ser Trp Glu Asp Met Gln Asn Glu Ile Thr Ser Phe Asp Thr
100 105 110

Val Glu Asp Phe Trp Ser Leu Tyr Asn His Ile Lys Pro Pro Ser Glu
115 120 125

Ile Lys Leu Gly Ser Asp Tyr Ser Leu Phe Lys Lys Asn Ile Arg Pro
130 135 140

Met Trp Glu Asp Ala Ala Asn Lys Gln Gly Gly Arg Trp Val Ile Thr
145 150 155 160

Leu Asn Lys Ser Ser Lys Thr Asp Leu Asp Asn Leu Trp Leu Asp Val
165 170 175

Leu Leu Cys Leu Ile Gly Glu Ala Phe Asp His Ser Asp Gln Ile Cys
180 185 190

Gly Ala Val Ile Asn Ile Arg Gly Lys Ser Asn Lys Ile Ser Ile Trp
195 200 205

Thr Ala Asp Gly Asn Asn Glu Glu Ala Ala Leu Glu Ile Gly His Lys
210 215 220

Leu Arg Asp Ala Leu Arg Leu Gly Arg Asn Asn Ser Leu Gln Tyr Gln
225 230 235 240

Leu His Lys Asp Thr Met Val Lys Gln Gly Ser Asn Val Lys Ser Ile
245 250 255

Tyr Thr Leu ( 2 ) INFORMATION FOR SEQ ID NO:7:

( i ) SEQUENCE CHARACTERISTICS:
( A ) LENGTH: 213 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:7:

Met Ser Val Glu Glu Val Ser Lys Lys Phe Glu Glu Asn Val Ser Val
1 5 10 15

Asp Asp Thr Thr Ala Thr Pro Lys Thr Val Leu Ser Asp Ser Ala His
20 25 30

Phe Asp Val Lys His Pro Leu Asn Thr Lys Trp Thr Leu Trp Tyr Thr
35 40 45

Lys Pro Ala Val Asp Lys Ser Glu Ser Trp Ser Asp Leu Leu Arg Pro
50 55 60

Val Thr Ser Phe Gln Thr Val Glu Glu Phe Trp Ala Ile Ile Gln Asn
65 70 75 80

Ile Pro Glu Pro His Glu Leu Pro Leu Lys Ser Asp Tyr His Val Phe
85 90 95

Arg Asn Asp Val Arg Pro Glu Trp Glu Asp Glu Ala Asn Ala Lys Gly
100 105 110

Gly Lys Trp Ser Phe Gln Leu Arg Gly Lys Gly Ala Asp Ile Asp Glu
115 120 125

Leu Trp Leu Arg Thr Leu Leu Ala Val Ile Gly Glu Thr Ile Asp Glu
130 135 140

Asp Asp Ser Gln Ile Asn Gly Val Val Leu Ser Ile Arg Lys Gly Gly
145 150 155 160

Asn Lys Phe Ala Leu Trp Thr Lys Ser Glu Asp Lys Glu Pro Leu Leu
165 170 175

Arg Ile Gly Gly Lys Phe Lys Gln Val Leu Lys Leu Thr Asp Asp Gly
180 185 190

His Leu Glu Phe Phe Pro His Ser Ser Ala Asn Gly Arg His Pro Gln
195 200 205

Pro Ser Ile Thr Leu
210

( 2 ) INFORMATION FOR SEQ ID NO:8:

( i ) SEQUENCE CHARACTERISTICS:
( A ) LENGTH: 218 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:8:

Met Gln Thr Glu Gln Pro Pro Lys Glu Ser Gln Thr Glu Asn Thr Val
1 5 10 15

Ser Glu Pro Gln Glu Lys Ala Leu Arg Thr Val Phe Asp Asp Lys Ile
20 25 30

Asn Phe Asn Leu Lys His Pro Leu Ala Arg Pro Trp Thr Leu Trp Phe
35 40 45

Leu Met Pro Pro Thr Pro Gly Leu Glu Trp Asn Glu Leu Gln Lys Asn
50 55 60

Ile Ile Thr Phe Asn Ser Val Glu Glu Phe Trp Gly Ile His Asn Asn
65 70 75 80

Ile Asn Pro Ala Ser Ser Leu Pro Ile Lys Ser Asp Tyr Ser Phe Phe
85 90 95

Arg Glu Gly Val Arg Pro Glu Trp Glu Asp Val His Asn Lys Thr Gly
100 105 110

Gly Lys Trp Ala Phe Gln Asn Lys Gly Arg Gly Gly Asn Ala Leu Asp
115 120 125

Glu Met Trp Leu Thr Thr Val Leu Ala Ala Ile Gly Glu Thr Leu Asp
130 135 140

Pro Thr Gly Gln Glu Val Met Gly Val Val Ile Asn Met Arg Lys Gly
145 150 155 160

Phe Tyr Arg Leu Ala Val Trp Thr Lys Ser Cys Asn Asn Arg Glu Val
165 170 175

Leu Met Glu Ile Gly Thr Arg Phe Lys Gln Val Leu Asn Leu Pro Arg
180 185 190

Ser Glu Thr Ile Glu Phe Ser Ala His Glu Asp Ser Ser Lys Ser Gly
195 200 205

Ser Thr Arg Ala Lys Thr Arg Met Ser Val
210 215

( 2 ) INFORMATION FOR SEQ ID NO:9:

( i ) SEQUENCE CHARACTERISTICS:
( A ) LENGTH: 209 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:9:

Met Ala Glu Val Glu Ala Ala Leu Pro Val Ala Ala Thr Glu Thr Pro
1 5 10 15

Glu Val Ala Ala Glu Ser Asp Ala Gly Ala Ala Glu Ala Lys Gly Pro
20 25 30

His Lys Leu Gln Arg Gln Trp Thr Phe Trp Tyr Asp Ile Gln Thr Lys
35 40 45

Pro Lys Pro Gly Ala Ala Trp Gly Thr Ser Leu Lys Lys Gly Tyr Thr
50 55 60

Phe Asp Thr Val Glu Glu Phe Trp Cys Leu Tyr Asp Gln Ile Phe Arg
65 70 75 80

Pro Ser Lys Leu Val Gly Ser Ala Asp Phe His Leu Phe Lys Ala Gly
85 90 95

Val Glu Pro Lys Trp Glu Asp Pro Glu Cys Ala Asn Gly Gly Lys Trp
100 105 110

Thr Val Ile Ser Ser Arg Lys Ala Asn Leu Asp Thr Met Trp Leu Glu
115 120 125

Thr Cys Met Ala Leu Ile Gly Glu Gln Phe Asp Glu Ser Gln Glu Ile
130 135 140

Cys Gly Val Val Ala Ser Val Arg Gln Arg Gln Asp Lys Leu Ser Leu
145 150 155 160

Trp Thr Lys Thr Ala Ser Asn Glu Ala Val Gln Val Asp Ile Gly Lys
165 170 175

Lys Trp Lys Glu Val Ile Asp Tyr Asn Asp Lys Met Val Tyr Ser Phe
180 185 190

His Asp Asp Ser Arg Ser Gln Lys Pro Ser Arg Gly Gly Arg Tyr Thr
195 200 205

Val (2) INFORMATION FOR SEQ ID NO:10:

(i) SEQUENCE CHARACTERISTICS:
(A) LENGTH: 182 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:10:

```
Lys His Pro Leu Gln Asn Arg Trp Ala Leu Trp Phe Phe Lys Asn Asp
1               5                   10                  15

Lys Ser Lys Thr Trp Gln Ala Asn Leu Arg Leu Ile Ser Lys Phe Asp
            20                  25                  30

Thr Val Glu Asp Phe Trp Ala Leu Tyr Asn His Ile Gln Leu Ser Ser
        35                  40                  45

Asn Leu Met Pro Gly Cys Asp Tyr Ser Leu Phe Lys Asp Gly Ile Glu
    50                  55                  60

Pro Met Trp Glu Asp Glu Lys Asn Lys Arg Gly Gly Arg Trp Leu Ile
65                  70                  75                  80

Thr Leu Asn Lys Gln Gln Arg Arg Ser Asp Leu Asp Arg Phe Trp Leu
                85                  90                  95

Glu Thr Leu Leu Cys Leu Ile Gly Glu Ser Phe Asp Asp Tyr Ser Asp
            100                 105                 110

Asp Val Cys Gly Ala Val Val Asn Val Arg Ala Lys Gly Asp Lys Ile
        115                 120                 125

Ala Ile Trp Thr Thr Glu Cys Glu Asn Arg Asp Ala Val Thr His Ile
    130                 135                 140

Gly Arg Val Tyr Lys Glu Arg Leu Gly Leu Pro Pro Lys Ile Val Ile
145                 150                 155                 160

Gly Tyr Gln Ser His Ala Asp Thr Ala Thr Lys Ser Gly Ser Thr Thr
                165                 170                 175

Lys Asn Arg Phe Val Val
            180
```

(2) INFORMATION FOR SEQ ID NO:11:

(i) SEQUENCE CHARACTERISTICS:
(A) LENGTH: 182 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:11:

```
Lys His Pro Leu Gln Asn Arg Trp Ala Leu Trp Phe Phe Lys Asn Asp
1               5                   10                  15

Lys Ser Lys Thr Trp Gln Ala Asn Leu Arg Leu Ile Ser Lys Phe Asp
            20                  25                  30

Thr Val Glu Asp Phe Trp Ala Leu Tyr Asn His Ile Gln Leu Ser Ser
        35                  40                  45

Asn Leu Met Pro Gly Cys Asp Tyr Ser Leu Phe Lys Asp Gly Ile Glu
    50                  55                  60

Pro Met Trp Glu Asp Glu Lys Asn Lys Arg Gly Gly Arg Trp Leu Ile
65                  70                  75                  80
```

-continued

Thr Leu Asn Lys Gln Gln Arg Arg Ser Asp Leu Asp Arg Phe Trp Leu
85 90 95

Glu Thr Leu Leu Cys Leu Ile Gly Glu Ser Phe Asp Asp Tyr Ser Asp
100 105 110

Asp Val Cys Gly Ala Val Val Asn Val Arg Ala Lys Gly Asp Lys Ile
115 120 125

Ala Ile Trp Thr Thr Glu Cys Glu Asn Arg Glu Ala Val Thr His Ile
130 135 140

Gly Arg Val Tyr Lys Glu Arg Leu Gly Leu Pro Pro Lys Ile Val Ile
145 150 155 160

Gly Tyr Gln Ser His Ala Asp Thr Ala Thr Lys Ser Gly Ser Thr Thr
165 170 175

Lys Asn Arg Phe Val Val
180

( 2 ) INFORMATION FOR SEQ ID NO:12:

( i ) SEQUENCE CHARACTERISTICS:
( A ) LENGTH: 182 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:12:

Lys His Pro Leu Gln Asn Arg Trp Ala Leu Trp Phe Phe Lys Asn Asp
1 5 10 15

Lys Ser Lys Thr Trp Gln Ala Asn Leu Arg Leu Ile Ser Lys Phe Asp
20 25 30

Thr Val Glu Asp Phe Trp Ala Leu Tyr Asn His Ile Gln Leu Ser Ser
35 40 45

Asn Leu Met Pro Gly Cys Asp Tyr Ser Leu Phe Lys Asp Gly Ile Glu
50 55 60

Pro Met Trp Glu Asp Glu Lys Asn Lys Arg Gly Gly Arg Trp Leu Ile
65 70 75 80

Thr Leu Asn Lys Gln Gln Arg Arg Ser Asp Leu Asp Arg Phe Trp Leu
85 90 95

Glu Thr Leu Leu Cys Leu Ile Gly Glu Ser Phe Asp Asp Tyr Ser Asp
100 105 110

Asp Val Cys Gly Ala Val Val Asn Val Arg Ala Lys Gly Asp Lys Ile
115 120 125

Ala Ile Trp Thr Thr Glu Cys Glu Asn Arg Asp Ala Val Thr His Ile
130 135 140

Gly Arg Val Tyr Lys Glu Arg Leu Gly Leu Pro Pro Lys Ile Val Ile
145 150 155 160

Gly Tyr Gln Ser His Ala Asp Thr Ala Thr Lys Ser Gly Ser Thr Thr
165 170 175

Lys Asn Arg Phe Val Val
180

( 2 ) INFORMATION FOR SEQ ID NO:13:

( i ) SEQUENCE CHARACTERISTICS:
( A ) LENGTH: 182 amino acids
( B ) TYPE: amino acid
( C ) STRANDEDNESS: single (D) TOPOLOGY: linear (ii) MOLECULE TYPE: protein (iii) HYPOTHETICAL: NO (xi) SEQUENCE DESCRIPTION: SEQ ID NO:13:

```
Lys His Pro Leu Gln Asn Arg Trp Ala Leu Trp Phe Phe Lys Asn Asp
1               5                   10                  15
Lys Ser Lys Thr Trp Gln Ala Asn Leu Arg Leu Ile Ser Lys Phe Asp
            20                  25                  30
Thr Val Glu Asp Phe Trp Ala Leu Tyr Asn His Ile Gln Leu Ser Ser
        35                  40                  45
Asn Leu Met Pro Gly Cys Asp Tyr Ser Leu Phe Lys Asp Gly Ile Glu
    50                  55                  60
Pro Met Trp Glu Asp Glu Lys Asn Lys Arg Gly Gly Arg Trp Leu Ile
65                  70                  75                  80
Thr Leu Asn Lys Gln Gln Arg Arg Ser Asp Leu Asp Arg Phe Trp Leu
                85                  90                  95
Glu Thr Leu Leu Cys Leu Ile Gly Glu Ser Phe Asp Asp Tyr Ser Asp
            100                 105                 110
Asp Val Cys Gly Ala Val Val Asn Val Arg Ala Lys Gly Asp Lys Ile
        115                 120                 125
Ala Ile Trp Thr Thr Glu Cys Glu Asn Arg Asp Ala Val Thr His Ile
    130                 135                 140
Gly Arg Val Tyr Lys Glu Arg Leu Gly Leu Pro Pro Lys Ile Val Ile
145                 150                 155                 160
Gly Tyr Gln Ser His Ala Asp Thr Ala Thr Lys Ser Gly Ser Thr Thr
                165                 170                 175
Lys Asn Arg Phe Val Val
            180
```

(2) INFORMATION FOR SEQ ID NO:14:

(i) SEQUENCE CHARACTERISTICS:
(A) LENGTH: 182 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:14:

```
Lys His Pro Leu Gln Asn Arg Trp Ala Leu Trp Phe Phe Lys Asn Asp
1               5                   10                  15
Lys Ser Lys Thr Trp Gln Ala Asn Leu Arg Leu Ile Ser Lys Phe Asp
            20                  25                  30
Thr Val Glu Asp Phe Trp Ala Leu Tyr Asn His Ile Gln Leu Ser Ser
        35                  40                  45
Asn Leu Met Ser Gly Cys Asp Tyr Ser Leu Phe Lys Asp Gly Ile Glu
    50                  55                  60
Pro Met Trp Glu Asp Glu Lys Asn Lys Arg Gly Gly Arg Trp Leu Ile
65                  70                  75                  80
Thr Leu Asn Lys Gln Gln Arg Arg Asn Asp Leu Asp Arg Phe Trp Leu
                85                  90                  95
Glu Thr Leu Met Cys Leu Ile Gly Glu Ser Phe Asp Glu His Ser Asp
            100                 105                 110
```

-continued

| | | | | | | | | | | | | | | | |
|---|---|---|---|---|---|---|---|---|---|---|---|---|---|---|---|
| Asp | Val | Cys 115 | Gly | Ala | Val | Val | Asn 120 | Val | Arg | Ala | Lys | Gly 125 | Asp | Lys | Ile |
| Ala | Ile 130 | Trp | Thr | Thr | Glu | Phe 135 | Glu | Asn | Lys | Asp | Ala 140 | Val | Thr | His | Ile |
| Gly 145 | Arg | Val | Tyr | Lys | Glu 150 | Arg | Leu | Gly | Leu | Pro 155 | Ala | Lys | Val | Val | Ile 160 |
| Gly | Tyr | Gln | Ser | His 165 | Ala | Asp | Thr | Ala | Thr 170 | Lys | Ser | Gly | Ser | Thr 175 | Thr |
| Lys | Asn | Arg | Phe 180 | Val | Val | | | | | | | | | | |

( 2 ) INFORMATION FOR SEQ ID NO:15:

( i ) SEQUENCE CHARACTERISTICS:
( A ) LENGTH: 180 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:15:

| | | | | | | | | | | | | | | | |
|---|---|---|---|---|---|---|---|---|---|---|---|---|---|---|---|
| Lys 1 | His | Pro | Leu | Met 5 | Asn | Val | Trp | Thr | Leu 10 | Trp | Tyr | Leu | Glu | Asn 15 | Asp |
| Arg | Ser | Lys | Ser 20 | Trp | Glu | Asp | Met | Gln 25 | Asn | Glu | Ile | Thr | Ser 30 | Phe | Asp |
| Thr | Val | Glu 35 | Asp | Phe | Trp | Ser | Leu 40 | Tyr | Asn | His | Ile | Lys 45 | Pro | Pro | Ser |
| Glu | Ile 50 | Lys | Leu | Gly | Ser | Asp 55 | Tyr | Ser | Leu | Phe | Lys 60 | Lys | Asn | Ile | Arg |
| Pro 65 | Met | Trp | Glu | Asp | Ala 70 | Ala | Asn | Lys | Gln | Gly 75 | Gly | Arg | Trp | Val | Ile 80 |
| Thr | Leu | Asn | Lys | Ser 85 | Ser | Lys | Thr | Asp | Leu 90 | Asp | Asn | Leu | Trp | Leu 95 | Asp |
| Val | Leu | Leu | Cys 100 | Leu | Ile | Gly | Glu | Ala 105 | Phe | Asp | His | Ser | Asp 110 | Gln | Ile |
| Cys | Gly | Ala 115 | Val | Ile | Asn | Ile | Arg 120 | Gly | Lys | Ser | Asn | Lys 125 | Ile | Ser | Ile |
| Trp | Thr 130 | Ala | Asp | Gly | Asn | Asn 135 | Glu | Glu | Ala | Ala | Leu 140 | Glu | Ile | Gly | His |
| Lys 145 | Leu | Arg | Asp | Ala | Leu 150 | Arg | Leu | Gly | Arg | Asn 155 | Asn | Ser | Leu | Gln | Tyr 160 |
| Gln | Leu | His | Lys | Asp 165 | Thr | Met | Val | Lys | Gln 170 | Gly | Ser | Asn | Val | Lys 175 | Ser |
| Ile | Tyr | Thr | Leu 180 | | | | | | | | | | | | |

( 2 ) INFORMATION FOR SEQ ID NO:16:

( i ) SEQUENCE CHARACTERISTICS:
( A ) LENGTH: 178 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:16:

-continued

Lys His Pro Leu Asn Thr Lys Trp Thr Leu Trp Tyr Thr Lys Pro Ala
1 5 10 15

Val Asp Lys Ser Glu Ser Trp Ser Asp Leu Leu Arg Pro Val Thr Ser
20 25 30

Phe Gln Thr Val Glu Glu Phe Trp Ala Ile Ile Gln Asn Ile Pro Glu
35 40 45

Pro His Glu Leu Pro Leu Lys Ser Asp Tyr His Val Phe Arg Asn Asp
50 55 60

Val Arg Pro Glu Trp Glu Asp Glu Ala Asn Ala Lys Gly Gly Lys Trp
65 70 75 80

Ser Phe Gln Leu Arg Gly Lys Gly Ala Asp Ile Asp Glu Leu Trp Leu
85 90 95

Arg Thr Leu Leu Ala Val Ile Gly Glu Thr Ile Asp Glu Asp Asp Ser
100 105 110

Gln Ile Asn Gly Val Val Leu Ser Ile Arg Lys Gly Gly Asn Lys Phe
115 120 125

Ala Leu Trp Thr Lys Ser Glu Asp Lys Glu Pro Leu Leu Arg Ile Gly
130 135 140

Gly Lys Phe Lys Gln Val Leu Lys Leu Thr Asp Asp Gly His Leu Glu
145 150 155 160

Phe Phe Pro His Ser Ser Ala Asn Gly Arg His Pro Gln Pro Ser Ile
165 170 175

Thr Leu ( 2 ) INFORMATION FOR SEQ ID NO:17:

( i ) SEQUENCE CHARACTERISTICS:
( A ) LENGTH: 182 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:17:

Lys His Pro Leu Ala Arg Pro Trp Thr Leu Trp Phe Leu Met Pro Pro
1 5 10 15

Thr Pro Gly Leu Glu Trp Asn Glu Leu Gln Lys Asn Ile Ile Thr Phe
20 25 30

Asn Ser Val Glu Glu Phe Trp Gly Ile His Asn Asn Ile Asn Pro Ala
35 40 45

Ser Ser Leu Pro Ile Lys Ser Asp Tyr Ser Phe Phe Arg Glu Gly Val
50 55 60

Arg Pro Glu Trp Glu Asp Val His Asn Lys Thr Gly Gly Lys Trp Ala
65 70 75 80

Phe Gln Asn Lys Gly Arg Gly Gly Asn Ala Leu Asp Glu Met Trp Leu
85 90 95

Thr Thr Val Leu Ala Ala Ile Gly Glu Thr Leu Asp Pro Thr Gly Gln
100 105 110

Glu Val Met Gly Val Val Ile Asn Met Arg Lys Gly Phe Tyr Arg Leu
115 120 125

Ala Val Trp Thr Lys Ser Cys Asn Asn Arg Glu Val Leu Met Glu Ile
130 135 140

Gly Thr Arg Phe Lys Gln Val Leu Asn Leu Pro Arg Ser Glu Thr Ile
145 150 155 160

-continued

| | | | | | | | | | | | | | | | |
|---|---|---|---|---|---|---|---|---|---|---|---|---|---|---|---|
| Glu | Phe | Ser | Ala | His<br>165 | Glu | Asp | Ser | Ser | Lys<br>170 | Ser | Gly | Ser | Thr | Arg<br>175 | Ala |
| Lys | Thr | Arg | Met<br>180 | Ser | Val | | | | | | | | | | |

( 2 ) INFORMATION FOR SEQ ID NO:18:

( i ) SEQUENCE CHARACTERISTICS:
( A ) LENGTH: 178 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( x i ) SEQUENCE DESCRIPTION: SEQ ID NO:18:

| | | | | | | | | | | | | | | | |
|---|---|---|---|---|---|---|---|---|---|---|---|---|---|---|---|
| Pro<br>1 | His | Lys | Leu | Gln<br>5 | Arg | Gln | Trp | Thr | Phe<br>10 | Trp | Tyr | Asp | Ile | Gln<br>15 | Thr |
| Lys | Pro | Lys | Pro<br>20 | Gly | Ala | Ala | Trp | Gly<br>25 | Thr | Ser | Leu | Lys | Lys<br>30 | Gly | Tyr |
| Thr | Phe | Asp<br>35 | Thr | Val | Glu | Glu | Phe<br>40 | Trp | Cys | Leu | Tyr | Asp<br>45 | Gln | Ile | Phe |
| Arg | Pro<br>50 | Ser | Lys | Leu | Val | Gly<br>55 | Ser | Ala | Asp | Phe | His<br>60 | Leu | Phe | Lys | Ala |
| Gly<br>65 | Val | Glu | Pro | Lys | Trp<br>70 | Glu | Asp | Pro | Glu | Cys<br>75 | Ala | Asn | Gly | Gly | Lys<br>80 |
| Trp | Thr | Val | Ile | Ser<br>85 | Ser | Arg | Lys | Ala | Asn<br>90 | Leu | Asp | Thr | Met | Trp<br>95 | Leu |
| Glu | Thr | Cys | Met<br>100 | Ala | Leu | Ile | Gly | Glu<br>105 | Gln | Phe | Asp | Glu | Ser<br>110 | Gln | Glu |
| Ile | Cys | Gly<br>115 | Val | Val | Ala | Ser | Val<br>120 | Arg | Gln | Arg | Gln | Asp<br>125 | Lys | Leu | Ser |
| Leu | Trp<br>130 | Thr | Lys | Thr | Ala | Ser<br>135 | Asn | Glu | Ala | Val | Gln<br>140 | Val | Asp | Ile | Gly |
| Lys<br>145 | Lys | Trp | Lys | Glu | Val<br>150 | Ile | Asp | Tyr | Asn | Asp<br>155 | Lys | Met | Val | Tyr | Ser<br>160 |
| Phe | His | Asp | Asp | Ser<br>165 | Arg | Ser | Gln | Lys | Pro<br>170 | Ser | Arg | Gly | Gly | Arg<br>175 | Tyr |
| Thr | Val | | | | | | | | | | | | | | |